(12) United States Patent
Herskovic et al.

(10) Patent No.: US 11,930,261 B2
(45) Date of Patent: Mar. 12, 2024

(54) INSERTION SHAFT FOR AN ELECTRICALLY ACTUATED SCOPE

(71) Applicant: Guidance Airway Solutions, LLC, Naperville, IL (US)

(72) Inventors: Joshua Joseph Herskovic, Boca Raton, FL (US); Mark A. Gummin, Silverton, OR (US); Thomas Franklin Harter, Naperville, IL (US)

(73) Assignee: Guidance Airway Solutions, LLC, Naperville, IL (US)

( * ) Notice: Subject to any disclaimer, the term of this patent is extended or adjusted under 35 U.S.C. 154(b) by 0 days.

(21) Appl. No.: 18/058,518

(22) Filed: Nov. 23, 2022

(65) Prior Publication Data

US 2023/0164419 A1 May 25, 2023

Related U.S. Application Data

(60) Provisional application No. 63/280,242, filed on Nov. 23, 2021.

(51) Int. Cl.
| | |
|---|---|
| *H04N 23/50* | (2023.01) |
| *B25J 9/10* | (2006.01) |
| *B25J 18/06* | (2006.01) |
| *G06F 3/01* | (2006.01) |
| *H04N 7/18* | (2006.01) |
| *A61B 1/005* | (2006.01) |

(52) U.S. Cl.
CPC .......... *H04N 23/555* (2023.01); *B25J 9/1085* (2013.01); *B25J 18/06* (2013.01); *G06F 3/017* (2013.01); *H04N 7/18* (2013.01); *A61B 1/0055* (2013.01); *A61B 1/0057* (2013.01); *A61B 1/0058* (2013.01)

(58) Field of Classification Search
None
See application file for complete search history.

(56) References Cited

U.S. PATENT DOCUMENTS

| | | | | |
|---|---|---|---|---|
| 2006/0282115 | A1* | 12/2006 | Abrams | ........... A61B 17/12022 606/200 |
| 2007/0132551 | A1* | 6/2007 | Mozer | ................ G07C 9/00563 70/277 |
| 2015/0190221 | A1* | 7/2015 | Schaefer | ................. A61F 2/915 623/1.11 |

(Continued)

*Primary Examiner* — Talha M Nawaz
(74) *Attorney, Agent, or Firm* — Michael D. Eisenberg

(57) ABSTRACT

An insertion shaft for an electrically actuated scope includes at least two wires. Each wire has a proximal end anchored to a respective proximal anchoring point and a distal end anchored to a respective distal anchoring point. The wires are disposed around a central axis and extend along the insertion shaft. Each of the wires comprises two-way memory material configured to contract when heated to or above a first predetermined temperature and return to a predetermined original length thereof upon cooling to or below a second predetermined temperature below the first predetermined temperature. The length of each wire is larger than a length along the insertion shaft between the proximal anchoring point and the distal anchoring point to which the wire is anchored, such that each of the wires is incorporated in the insertion shaft with a predetermined slack.

30 Claims, 25 Drawing Sheets

(56) References Cited

U.S. PATENT DOCUMENTS

2015/0359487 A1* 12/2015 Coulombe ......... A61B 18/1492
600/375
2017/0047024 A1* 2/2017 Hogo ....................... H04N 5/64
2022/0071477 A1* 3/2022 Zaar .................... A61B 1/0057

* cited by examiner

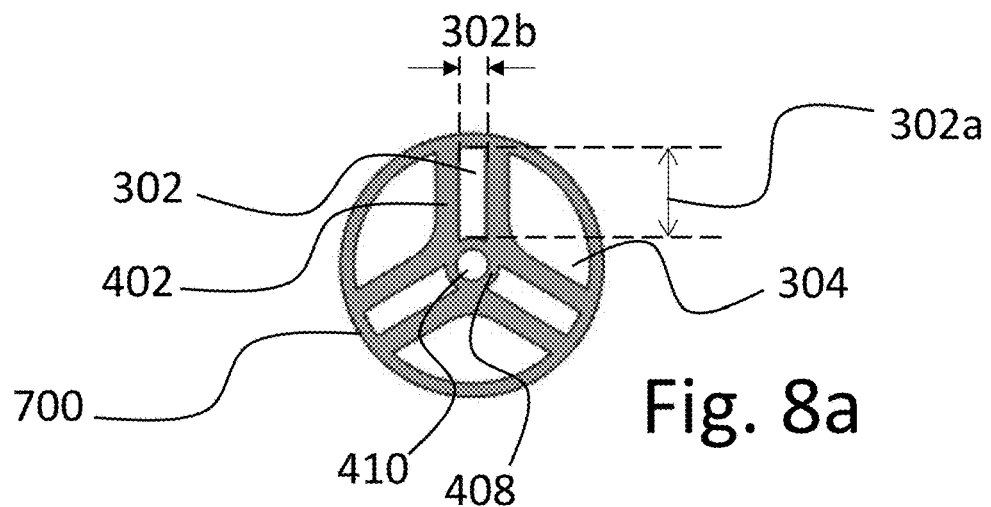
Fig. 8a
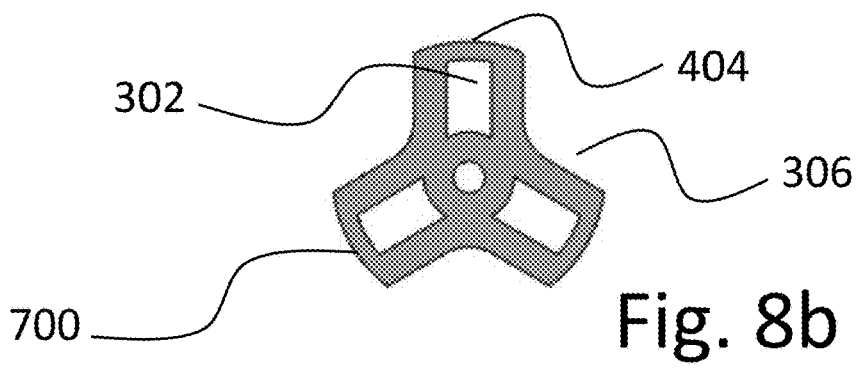
Fig. 8b
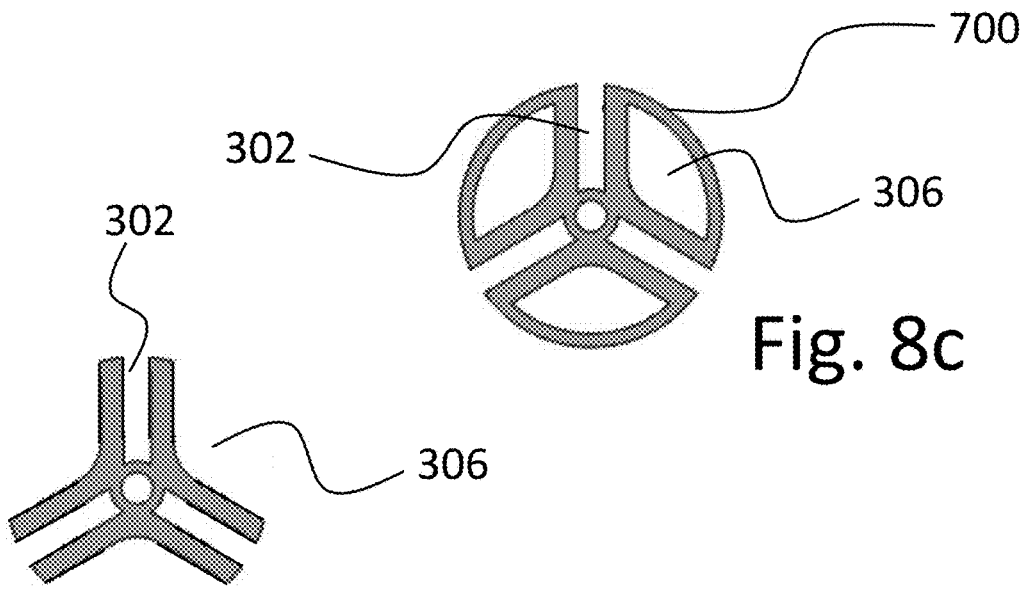
Fig. 8c
Fig. 8d

108

INSERTION SHAFT FOR AN ELECTRICALLY ACTUATED SCOPE

CROSS-REFERENCES TO RELATED APPLICATIONS

This application claims priority from U.S. Provisional Application Ser. No. 63/280,242 filed Nov. 23, 2021, which is hereby incorporated herein by reference in its entirety.

TECHNICAL FIELD

This invention relates to optical instruments designed to assist visual inspection of cavities. Such instruments may include, for example, borescopes and endoscopes.

BACKGROUND OF THE INVENTION

In medicine, instruments to be inserted in the body for inspection of desired body parts and body lumens and are referred to as endoscopes. In engineering, instruments to be inserted in cavities of machinery, building, or electronic apparatuses, for inspection of these cavities are referred to as bore scopes. Endoscopes and borescopes generally include cameras having digital imaging sensors, such as a CCD or CMOS sensor located at the distal end of a flexible cable, with an electrical wire to transmit the camera and light signal, and an outer sheath to allow for flexibility and protection of the inner wires.

The distal end of the flexible cable is generally fixed to a metallic wire, which runs the length of the flexible cable and is attached to one or more pulleys at proximal end. A lever is typically attached to the pulley(s) so that rotation of the lever results in rotation of the pulley. The rotation results in shortening of said metallic wire which is affixed to a flexible portion of the cable at the distal end of the cable. Thus, the rotation which results in flexion in a single axis of the flexible portion of the cable.

The pulley and lever system limits the reduction of size of the endoscope and the amount of axis the camera can flex about that can be incorporated into the flexible camera system.

BRIEF SUMMARY OF EMBODIMENTS OF THE INVENTION

Mechanical linkage with pulley system and lever is generally bulky and expensive to produce. Attempts to replace the system with motors instead of lever lead to large robots that take up an entire operating room.

An aim of the present invention is to provide an insertion shaft for a scope (e.g., endoscope or bore scope), which includes an electrical actuator, which enables flexion of the shaft by electrical means.

In this manner, the size of the insertions shaft of the present invention can reduced. Moreover, the insertion shaft can include a connector which enables the insertion shaft of the present invention to be separated from the head unit containing the electronics, controls, and imaging screen/LCD. An electrical connector generally has lower manufacture and production cost than a mechanical connection apparatus. Moreover, due to the simpler electrical connector of the insertion shaft of the present invention, the insertion shaft may be disposable.

Therefore, an aspect of some embodiments of the present invention relates to an insertion shaft for an electrically actuated scope. The insertion shaft includes at least two wires. Each wire has a proximal end and a distal end. Each proximal end is anchored to a respective proximal anchoring point located at a proximal end of the insertion shaft or at a predetermined location along the insertion shaft, and each distal ends is anchored to a respective distal anchoring point located between a distal end of the insertion shaft and the proximal anchoring point. The wires are disposed around a central axis and extend along the insertion shaft. Each of the wires comprises two-way memory material configured to contract when heated to or above a first predetermined temperature and return to a predetermined original length thereof upon cooling to or below a second predetermined temperature below the first predetermined temperature. The length of each wire is larger than a length along the insertion shaft between the proximal anchoring point and the distal anchoring point to which the wire is anchored, such that each of the wires is incorporated in the insertion shaft with a predetermined slack. The insertion shaft is configured to be joined to a control apparatus, such that each wire is configured to be independently and selectively heated by application of electrical current from the control apparatus, to yield a bending of the bendable portion.

In a variant, the insertion shaft further comprises a central wire or central spring disposed along the central axis, the central wire or central spring being elastic, such that the central wire or central spring is configured to maintain the insertion shaft unbent when all the wires are at or below the second predetermined temperature.

The central wire or central spring may be a grounding wire electrically connected to the wires and configured to be connected to an electrical ground.

In some embodiments of the present invention, a bendable portion of the insertion shaft located between the proximal anchoring point and the distal anchoring point comprises a frame, comprising a plurality of discrete slots and one or more hollos spaces. Each slot is elongated and has a large dimension and a small dimension, the large dimension extending substantially radially or with a radial component from the central axis. Each slot is traversed by a respective one of the wires and enables movement of the wire along the large dimension. The one or more hollow spaces are configured to be traversed by wiring and/or piping for tools held by the insertion shaft.

In a variant, the frame comprises a plurality of segments spaced-apart along the central axis of the insertion shaft. Each segment includes a central hub and a plurality of arms. The central hub is located in middle of the segment and is centered about the central axis of the insertion shaft. The plurality of arms extend substantially radially outward from the central hub. The slots being carved out of the arms and the hollow spaces are disposed between the arms. A distance between the segments is selected to enable an orientation change between successive segments.

In another variant, the insertion shaft further comprises a central wire or central spring disposed along the central axis, the central wire or central spring being elastic, such that the central wire or central spring is configured to maintain the insertion shaft unbent when all the wires are at or below the second predetermined temperature. The central hub of each segment has a central perforation configured to be traversed by the central wire or central spring.

In yet another variant, the frame comprises a plurality of segments spaced-apart along the central axis of the insertion shaft, each segment comprising a plurality of arms extending substantially radially or with a radial component inward from a perimeter of the frame. The slots are carved out of the arms. The hollow spaces are disposed between the arms.

In a further variant, any two successive segments share a central core and are separated by a gap extending radially from the perimeter of the frame toward the central core.

In yet a further variant, the frame is helical and has a radial thickness extending inward from a perimeter to the frame, such that the slots are carved out of the radial thickness.

In a variant, the slots have straight or curved shapes.

In another variant, frame has a continuous perimeter ridge which encloses the slots and the hollow spaces.

In yet another variant, the frame has a non-continuous perimeter ridge which encloses the hollow spaces, but is open at the slots. The insertion shaft comprises a flexible outer sheath enclosing the frame, to prevent the wires from radially exiting the slots.

In a further variant, the frame has a non-continuous perimeter ridge which encloses the slots, but is open at the hollow spaces. The insertion shaft comprises a flexible outer sheath enclosing the segments, to prevent the wiring and/or piping from radially exiting the hollow spaces.

In some embodiments of the present invention, a portion between the bending portion and the proximal end of the insertion shaft comprises a flexible central core shaft extending along the central axis of the insertion shaft and configured for guiding the wires therethrough.

In a variant, the insertion shaft further comprises a plurality of sets of arms extending substantially radially outward from the central core shaft, the arms having same longitudinal dimensions extending parallel to the central core shaft. The sets of arms are spaced apart by respective gaps. In each set of the arms a space between a pair of arms is traversed by a respective wire or by an electrical lead connected to the wire.

In another variant, the central core shaft has a central perforation.

In yet another variant, the central core shaft and frame are integral with each other.

In a variant, each wire loops about a respective distal looping point and returns toward the respective proximal anchoring point.

In another variant, at least one of the wires is in a form a helical coil extending substantially parallel to the central axis.

In yet another variant, the insertion shaft comprises at least three wires.

In a further variant, the insertion shaft includes an electrical valve configured to control an operation of a tool joined to the insertion shaft, the electrical valve being configured to be connected to the control unit and to be controlled by the control unit.

According to some embodiments of the present invention, a scope is provided, comprising the insertion shaft described above and a control unit. The control unit is configured to receive a user instruction to bend the insertion shaft in a desired direction, and to independently and selectively heat each of the wires to the predetermined temperature by applying electrical current via each of the wires, thereby controlling a length of each of the wires, to control a bending of the bendable portion of the insertion shaft according to the user instruction.

In a variant, the control unit comprises: a user interface, for receiving the user instructions; a memory utility configured to store predetermined commands; a power transmission unit configured to selectively and independently apply the electrical current to each one of the wires; a processor, configured to receive the user instructions and to use the predetermined commands to translate the user instructions to generate control signals that controls an operation of the power transmission unit in order to bend the insertion shaft according to the user instructions.

In another variant, the scope comprises a camera located at the distal end of the insertion shaft, the camera being configured to capture an image and generate electrical signals indicative of the image. The control unit is configured to be connected to a display by wire or wirelessly, and to transmit the electrical signals from the camera to the display, to enable the display to display the image.

In yet another variant, the scope includes the display, wherein the display is configured to be removably joined to the control unit.

In a further variant, the insertion shaft comprises a connector at the proximal end thereof and is removably joined to the control unit via a connector.

In yet a further variant, the user interface comprises a camera with an image processing unit configured to translate hand signals into electronic signals for bending the shaft.

In a variant, the scope includes a camera and the user interface includes an image processing unit. The camera is located at a distal end of the insertion shaft and pointing ahead of the insertion shaft. The image processing unit configured to keep the camera to be centered in a lumen in which the insertion shaft travels, and to automatically bend the shaft to maintain the camera position in the center of the lumen throughout the travel of the lumen.

Another aspect of some embodiments of the present invention relates to an insertion shaft for an electrically actuated scope, the insertion shaft comprising: The insertion shaft includes at least two wires. Each wire has a proximal end and a distal end. Each proximal end is anchored to a respective proximal anchoring point located at a proximal end of the insertion shaft or at a predetermined location along the insertion shaft, and each distal ends is anchored to a respective distal anchoring point located between a distal end of the insertion shaft and the proximal anchoring point. The wires are disposed around a central axis and extend along the insertion shaft. Each of the wires comprises two-way memory material configured to contract when heated to or above a first predetermined temperature and return to a predetermined original length thereof upon cooling to or below a second predetermined temperature below the first predetermined temperature. A bendable portion of the insertion shaft located between the proximal anchoring point and the distal anchoring point comprises a frame, comprising a plurality of discrete slots and one or more hollow spaces. Each of discrete slots is elongated and having a large dimension and a small dimension, the large dimension extending substantially radially or with a radial component from the central axis, each slot being traversed by a respective one of the wires and enabling movement of the wire along the large dimension. The one or more hollow spaces are configured to be traversed by wiring and/or piping for tools held by the insertion shaft. The insertion shaft is configured to be joined to a control apparatus, such that each wire is configured to be independently and selectively heated by application of electrical current from the control apparatus, to yield a bending of the bendable portion.

In a variant, for each of the wires, a length of the wire is larger than a length along the insertion shaft between the proximal anchoring point and the distal anchoring point to which the wire is anchored, such that each of the wires is incorporated in the insertion shaft with a predetermined slack.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIGS. 8a-8h are front cross-sectional views of differently shaped segments for the retention of the SMA wires of the insertion shaft, according to some embodiments of the present invention;

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1A:
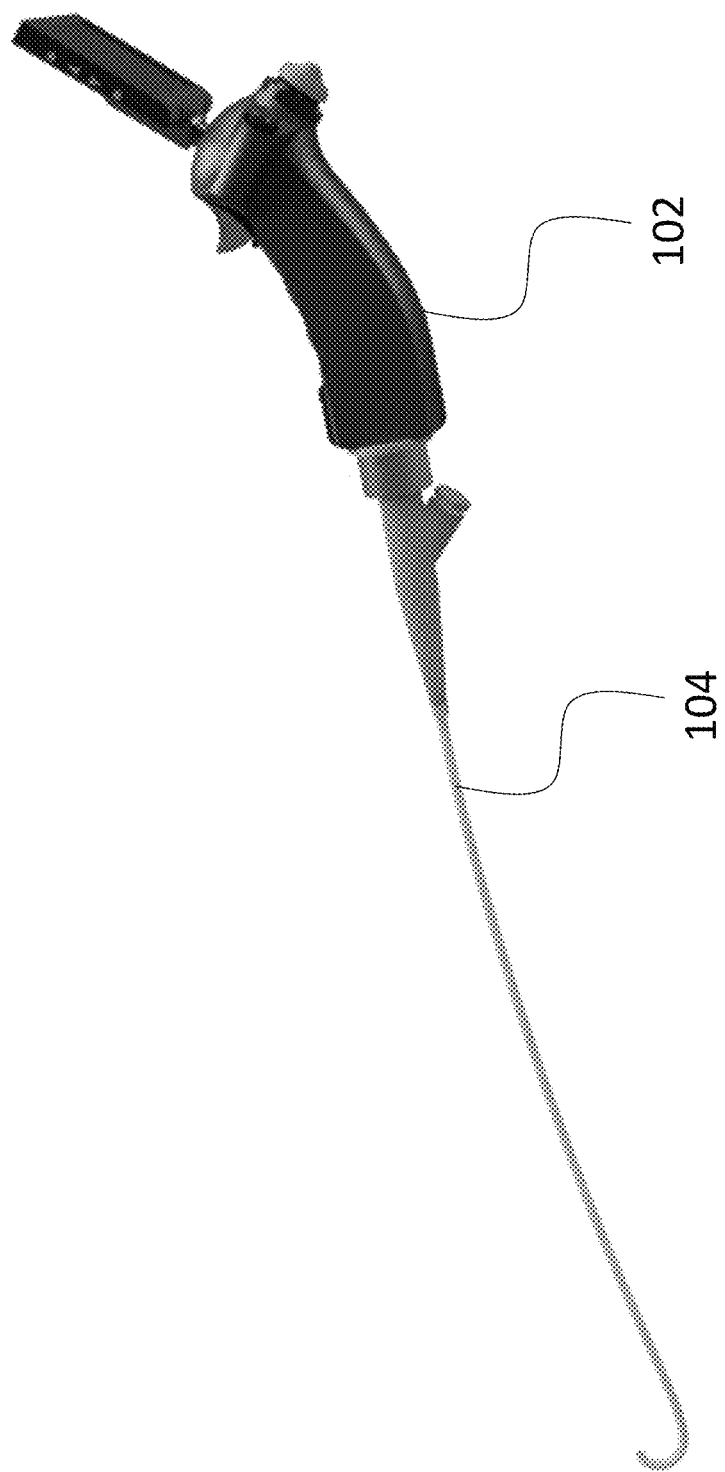
FIG. 1a shows a scope including an insertion shaft, according to some embodiments of the present invention.
Figure 1B:
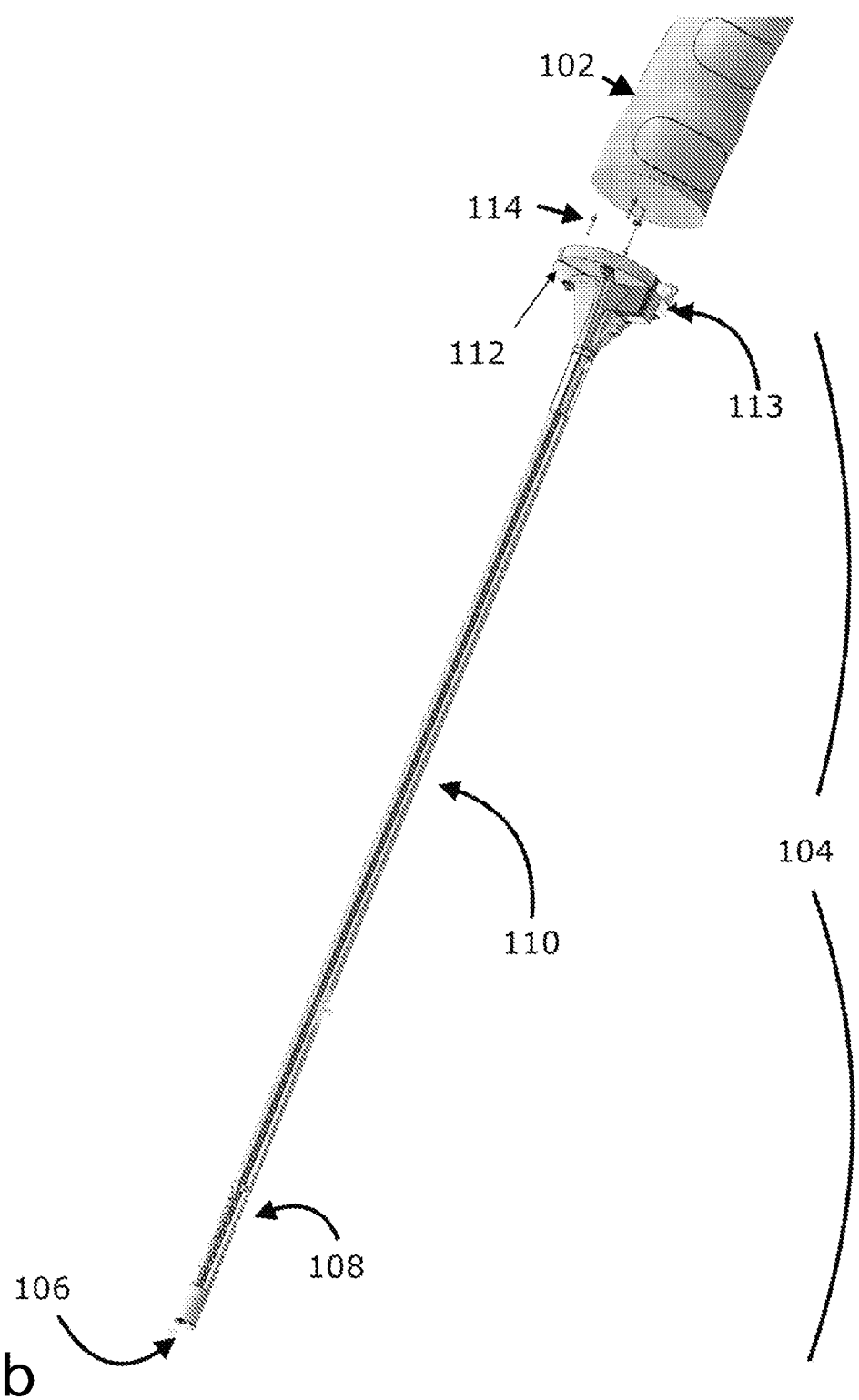
FIG. 1b shows some detail of the insertion shaft of the present invention.

FIG. 1a shows a scope 100 including an insertion shaft 104, according to some embodiments of the present invention. FIG. 1b shows some detail of the insertion shaft of the present invention.

The scope 100 includes a control unit 102 and an insertion shaft 104. The insertion shaft includes a distal portion 106 (distal from the control unit 102), a bendable portion 108 extending proximally from the distal portion 106, and a proximal portion 110 extending proximally from the bendable portion 108. The proximal portion 110 is connected to the control unit 102 via a connector base 112 having electronic connection pins 114 which connect the electrical SMA wires (which will be described further below) to the control unit 102 (which will also be described in detail further below), to enable control of the bendable portion 108 via the control unit 102.

Figure 2A:
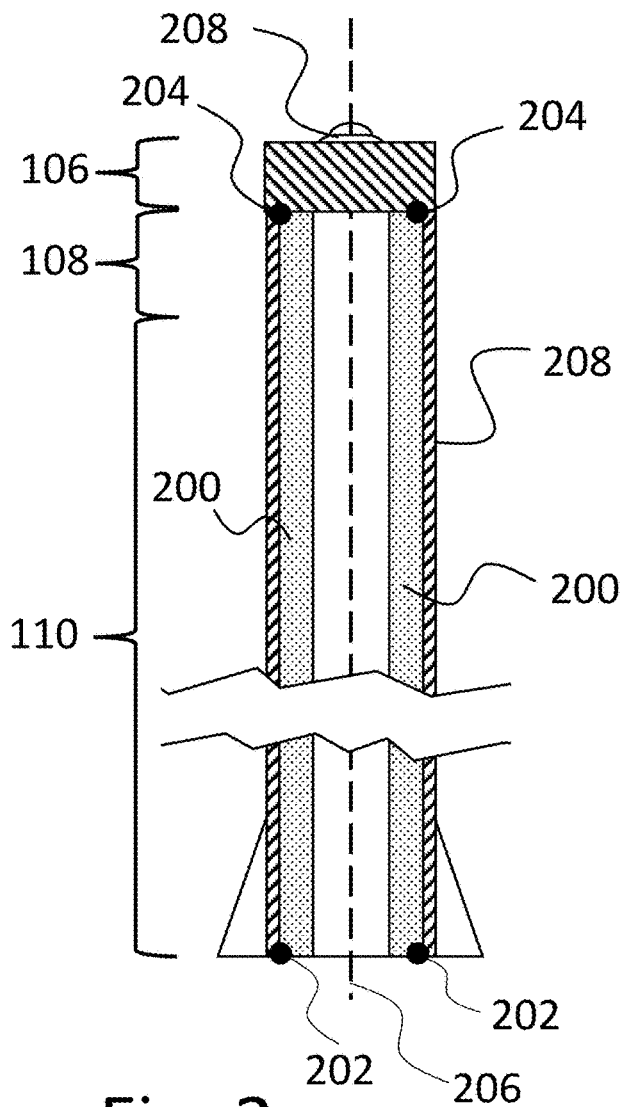
FIGS. 2a-2c are schematic drawings illustrating a principle of operation of the insertion shaft of the present invention.
Figure 2B:
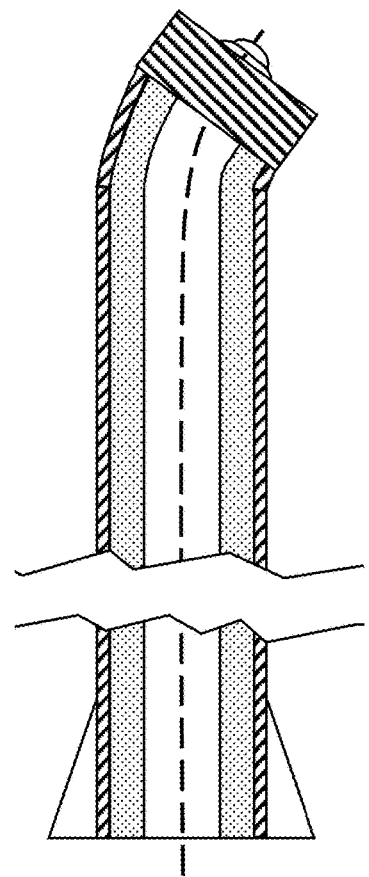
Figure 2C:
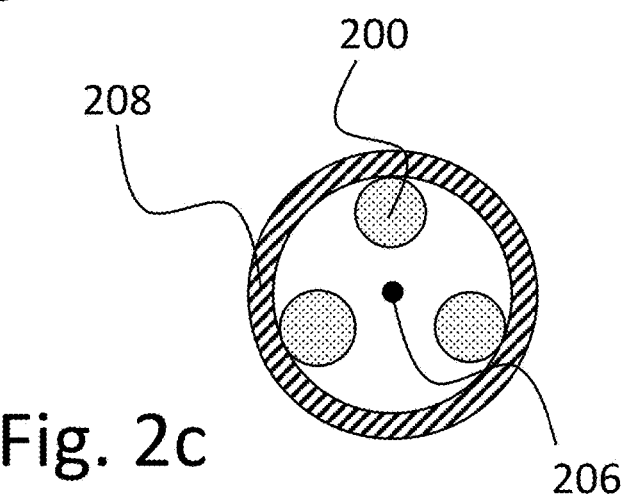
Figure 3:
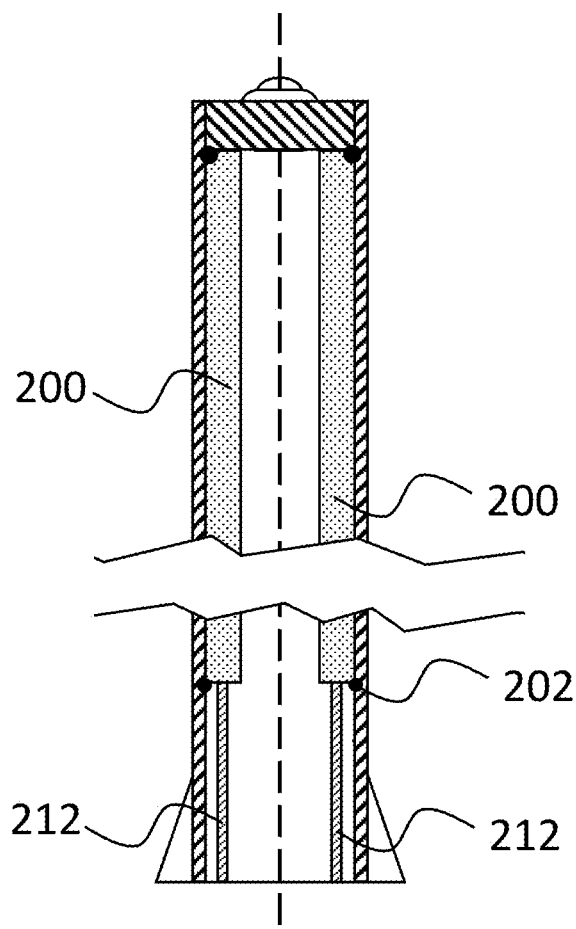
FIG. 3 is a schematic drawing illustrating an insertion shaft with electrical leads connecting to shape memory actuator (SMA) wires, according to some embodiments of the present invention.

FIGS. 2a-2c are schematic drawings illustrating a principle of operation of the insertion shaft 102 of the present invention. FIG. 3 is a schematic drawing illustrating an insertion shaft with electrical leads connecting to shape memory actuator (SMA) wires, according to some embodiments of the present invention.

The insertion shaft 104 includes at least two SMA wires 200. Each of the SMA wires 200 has a proximal end anchored to a proximal anchoring point 202 located at a proximal end of the insertion shaft (as seen in FIG. 2a) or at a predetermined location along the insertion shaft (as seen in FIG. 3) and a distal end anchored to a distal anchoring point 204 located between a distal end of the insertion shaft and the proximal anchoring point 202. Generally, the distal anchoring point is at or near the distal end of the bending portion 108. The wires extend along the insertion shaft 104 and may be substantially parallel to a central (longitudinal) axis 204 along which the insertion shaft 104 extends. The insertion shaft 104 may include a flexible sheath 208 to enclose the SMA wires 200.

Each of the SMA wires 200 comprises two-way memory material configured to contract when heated to or above a first predetermined temperature and return to a predetermined original length thereof upon cooling to or below a second predetermined temperature below the first predetermined temperature. The two-way memory material may be, for example, nitinol or a variant of nitinol incorporating an additional or similar behaving alloys such as NiTiCu. The SMA wires 200 may be in the form of straight filament or a coil. In a non-limiting example, the SMA wires 200 may have a diameter ranging between 0.03 mm and 1 mm.

The insertion shaft 104 is configured to be joined to a control (102, in FIGS. 1a and 1b), such that each SMA wire is configured to be independently and selectively heated by application of electrical current from the control unit, to yield a bending of the bendable portion.

As shown in FIG. 2b, the right-hand-side SMA wire 200 is heated and contracts, while the left-hand side SMA wire 200 is not heated and therefore remains at its original length. This causes the bendable portion 108 to bend to the right. The distal portion 106, therefore rotates to the right. The distal portion 106 generally includes a camera 208. Thus, the camera is rotated.

In some embodiments of the present invention, each of the SMA wires 200 is incorporated in the insertion shaft 104 with a predetermined slack. Thus, a length of each SMA wire 200 is larger than a length along the insertion shaft between the proximal anchoring point 202 and the distal anchoring point 204. Materials like nitinol are essentially inelastic beyond their original length. Therefore, when one of the SMA wires contacts, the rotation of the distal portion 106 would be limited if the opposing SMA wire did not have any slack. As one of the wires contracts the slack of the opposing wire enables the opposing wire to fully stretch to its original length (which is longer than the distance between the anchoring points 202 and 204) and therefore enables the contracted SMA wire to apply torque on the distal portion 106 with resistance from the opposing SMA wire occurring only after the opposing SMA wire has stretched from a slack configuration to a taught configuration at its original length.

Another advantage of having slack in the SMA wires 200 lies in the responsiveness of the insertion shaft to commands to change direction. After the SMA is no longer heated the SMA wire cools down and returns to its slack configuration. Because of the returning slack in the cooling wire, the opposing wire can be activated (heated) to change the direction of the distal portion 106 and the camera even before the cooling wire has fully cooled. Therefore, the insertion shaft 102 is more responsive to commands and direction changes.

FIGS. 2a and 2b show an embodiment in which two SMA wires 200 are present. However, the scope of the present patent application extends to any number of SMA wire larger than two. In fact, in prototypes built by the inventors three or four wires were used. In the example in which three SMA wires 200 are present the SMA wires may be centered about the central axis 206, as seen in FIG. 2c.

In the example of FIG. 3, in which the proximal anchoring points 202 are not located at the proximal end of the insertion shaft 104, electrical leads 212 extend between the proximal end of the insertion shaft 104 to the SMA wires 200, in order to electrically connect the SMA wires to the control unit.

The length of the SMA wire depends on the diameter of the distal end of the bendable portion 108 or on the distance of the SMA wires 200 from the central axis. In a non-limiting example, for an insertion shaft in which the bendable portion has a diameter of about 6 mm diameter tip, the SMA wires may be roughly 2.5 mm away from the central axis. When the SMA wires are close to the axis, angular rotation is large at the expense of force as it requires an increased force to rotate the distal end of the insertion shaft tip when the SMA is close to the axis).

Due to the small contraction of the SMA wires (about 3.75%), a scope with a 6 mm diameter requires about 300 mm of SMA wire to produce a very large deflection angle of the distal portion 106 (exceeding 150 degrees).

When fully contracted, a 300 mm long SMA wire produces 11.25 mm of contraction, and only about 6-7 mm of that is needed for the 150-degree rotation. This leaves about 4-5 mm of 'slack' in the SMA wires, but only about 3.5-4.0 mm are needed for the small diameter shaft 104. Thus, in this example, the length of the SMA wire is 300 mm, which includes 3.5 to 5 mm of slack.

For a 12 mm shaft, the length of each SMA wires may be about 600 mm, producing 22.5 mm of useful (contraction). If the SMA wires are at a radius 5.5 mm from the central axis, estimates are that 6-7 mm of slack would be needed, with remainder producing full rotation. Thus, the length of the SMA wire is 600 mm, which includes 6-7 mm of slack.

Figure 4:
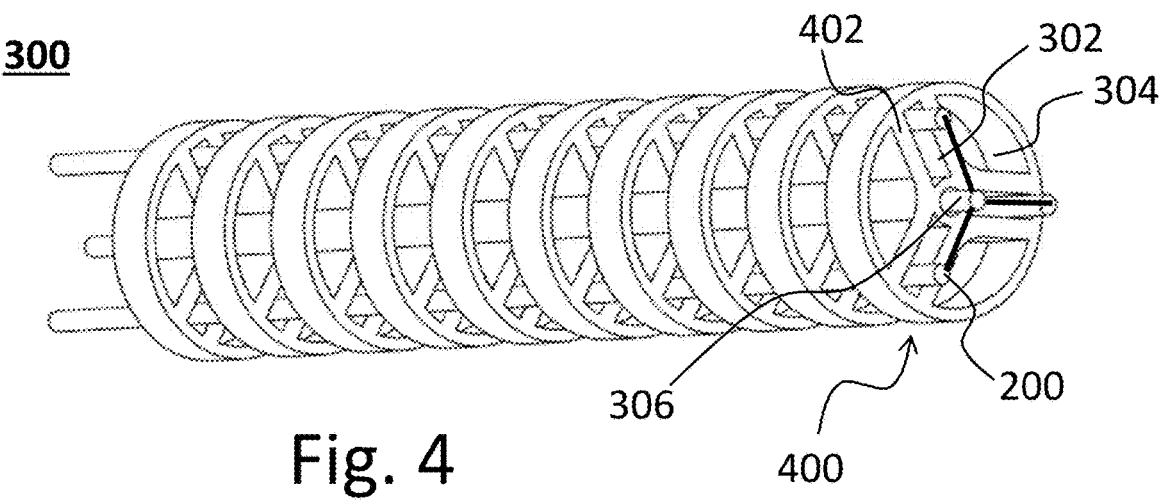
FIGS. 4 and 5 illustrate a bendable portion of the insertion shaft having a frame having a plurality of spaced-apart segments having a central hub, according to some embodiments of the present invention.
Figure 5:
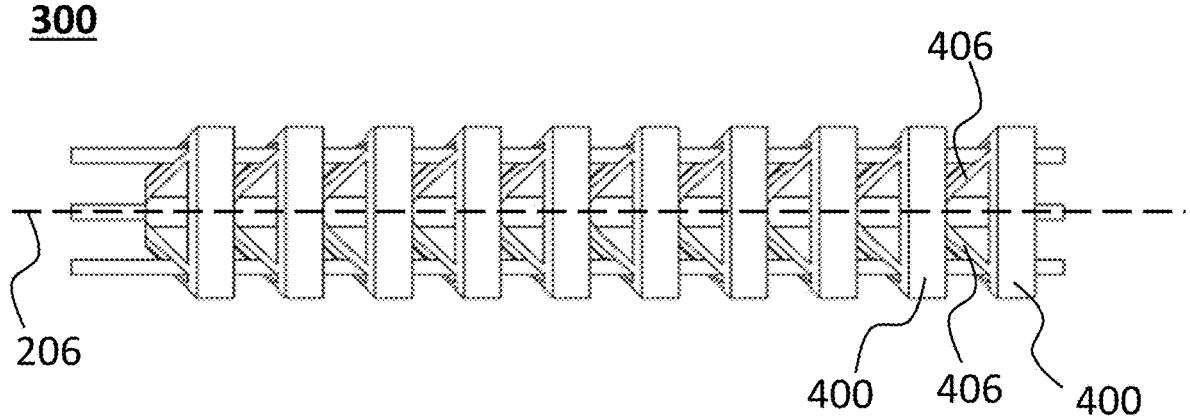
Figure 6:
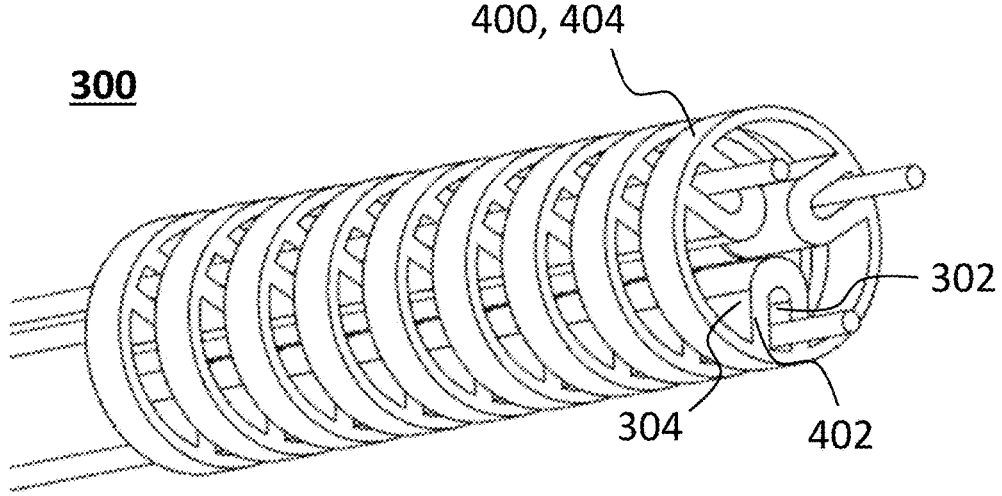
FIG. 6 illustrates a bendable portion of the insertion shaft having a frame having a plurality of spaced-apart segments not having a central hub, according to some embodiments of the present invention.
Figure 7:
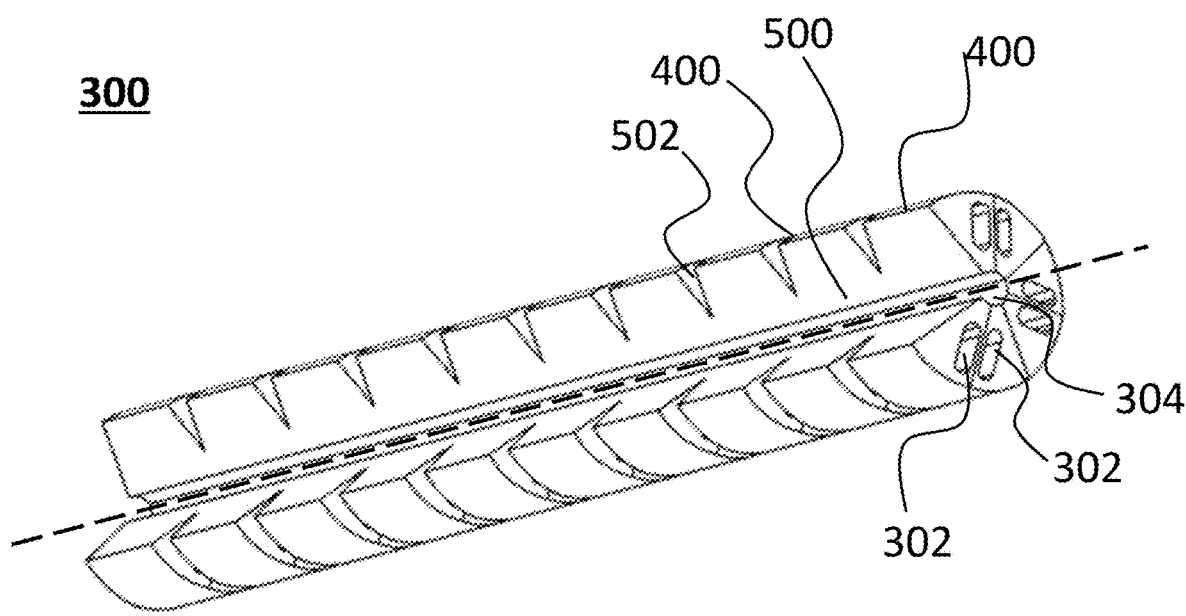
FIG. 7 illustrates a cut view of the bendable portion of the insertion shaft having a frame having a plurality of spaced-apart segments separated by a v-shaped notch, according to some embodiments of the present invention.

An aspect of the present invention relates to frame of the bendable portion 108. The features of the frame that will be discussed below may be an independent feature of the invention, in which the SMA wires may or may not have the slack described above. Reference is now made to FIGS. 4-9, which relate to this aspect of the invention. FIGS. 4 and 5 illustrate a bendable portion of the insertion shaft having a frame having a plurality of spaced-apart segments having a central hub, according to some embodiments of the present invention. FIG. 6 illustrates a bendable portion of the insertion shaft having a frame having a plurality of spaced-apart segments not having a central hub, according to some embodiments of the present invention. FIG. 7 illustrates a bendable portion of the insertion shaft having a frame having a plurality of spaced-apart segments separated by a notch, according to some embodiments of the present invention. FIGS. 8a-8h are front cross-sectional views of differently shaped segments for the retention of the SMA wires of the insertion shaft, according to some embodiments of the present invention. FIG. 9 illustrates a bendable portion of the insertion shaft having a helical frame.

The bendable portion 108 of the insertion shaft 104 is located in between the proximal anchoring points 202 and the distal anchoring points 204. It should be noted that the bendable portion need not encompass the entire distance between the proximal and distal anchoring points 202 and 204. The bendable portion 108 include a frame 300 which includes a plurality of discrete slots 302 and one or more hollow spaces 304.

Each slot 302 is elongated and has a large dimension 302a and a small dimension 302b, as shown in FIG. 8a and can be applied to all of FIGS. 4-9. The large dimension 302a extends substantially radially from the central axis 206. Each slot 302 is traversed by a respective one of the SMA wires 200 and the large dimension 302a is substantially larger than the diameter of the SMA wire 200, thereby enabling movement of the SMA wire 200 along the large dimension 302a. For example, if the SMA wire has a diameter between 0.03 mm and 0.5 mm, the large dimension may range between 2 mm and 6 mm. The small dimension 302b is chosen to be large enough not to prevent the SMA wire 200 from moving along the large dimension, yet small enough to prevent nearby wires from moving circumferentially and touching each other in the frame's gaps. In a non-limiting example, the small dimension 302b may be between 0.25 mm and 1 mm. The hollow space(s) 304 is (are) configured to be traversed by wiring and/or piping for tools held by the insertion shaft. The tools may include, for example, hollow tubing such as suction line to suction fluids from a lumen. The tool (e.g. suction line) may be electrically actuated via an electrical valve 113 located on the insertion shaft 104, as shown in FIG. 2. The electrical valve 113 is configured to be connected to the control unit 102 when the insertion shaft is connected to the control unit, and to be controlled by the control unit. The electrical valve is normally closed and provides connection from an external vacuum source and the suction line.

In some embodiments of the present invention, the insertion shaft includes a central wire or spring 306 disposed along the central axis. In an embodiment of the present invention, the central wire 306 is elastic, and as such returns to its original shape after and size deformation, when the forces causing the deformation are removed. Thus, the elastic central wire or spring is configured to maintain the insertion shaft unbent when all the SMA wires 200 are at or below the second predetermined temperature and exert no forces on distal anchoring points. Thus, the central wire or spring 306 provides a bias to return to a straight configuration and enhances the responsiveness to the bendable portion of the insertion shaft.

In some embodiments of the present invention the central wire is a grounding wire electrically connected to the SMA wires and configured to be connected to an electrical ground via the control unit. In this manner, current flowing through each SMA wire 200 is led to ground via the central wire 306.

In some embodiments of the present invention, as shown in FIGS. 4-7, the frame 300 includes a plurality of segments 400 spaced-apart along the central axis 206 of the insertion shaft. Each segment 400 includes a plurality of arms 402 extending substantially radially inward from a perimeter 404 of the segment 400. The slots 302 are carved out in the arms 402. The hollow spaces 304 are disposed between the arms. The distance between the segments is selected to enable an orientation change between successive segments.

In some embodiments of the present invention, the segments 400 are separated by flexible spacers 406 (as shown in FIG. 5), which enable the segments to rotate with respect to each other 400, to yield the bending of the bending portion. The segments and spacers may be made from a single material and may be integral with each other. It should be noted that the spacers are an optional feature. In some embodiments of the present invention, the entire frame in the bending portion can be made from an elastomer, such as silicone, for example.

In some embodiments of the present invention, as shown in FIG. 4, each segment 400 includes a central hub 408 and a plurality of arms 402. The central hub 408 is located in middle of the segment 400 and centered about the central axis 204 of the insertion shaft. The arms 402 extend substantially radially outward from the central hub 408, with the slots being carved in the arms 402. The central wire or spring 306 (if present) is accommodated in a central perforation 410 in the central hub.

In some embodiments of the present invention, as shown in FIG. 7, any two successive segments 400 share a central core 500 and are separated by a perimetral notch/gap 502 extending radially from the perimeter of the frame toward the central core 500. The notch/gap may have a v-shaped or u-shaped profile. Thus, the frame 300 is thinner between segments, and therefore more flexible in the thinner regions between segments. In this manner, the segments are rotatable with respect to each other. In the example of FIG. 4, the hollow space 304 traverses of the central core 500.

In some embodiments of the present invention, as shown in FIG. 9, the frame 300 is helical and has a radial thickness 600 extending inward from a perimeter 602 to the frame, such that the slots 302 are carved out of the radial thickness. The hollow space 304 is in the middle of the helix.

FIGS. 8a-8h are front cross-sectional views of differently shaped segments 400 for the retention of the SMA wires of the insertion shaft, according to some embodiments of the present invention.

In FIG. 8a, the frame has a continuous perimeter ridge 700, which encloses the slots 302 and the hollow spaces 304.

In FIG. 8b, the frame has a non-continuous perimeter ridge 700 which encloses the slots 302, but is open at the hollow spaces 304. The insertion shaft comprises a flexible outer sheath (208 in FIGS. 2a and 2c) enclosing the frame, to prevent the wiring and/or piping from radially exiting the hollow spaces.

In FIG. 8c, the frame has a non-continuous perimeter ridge 700 which encloses the hollow spaces 304, but is open at the slots 302. The insertion shaft comprises a flexible sheath (208 in FIGS. 2a and 2c) enclosing the frame, to prevent the SMA wires from radially exiting the slots.

In FIG. 8d, both the slots 302 and the hollow spaces 304 are open. The insertion shaft comprises a flexible sheath (208 in FIGS. 2a and 2c) enclosing the frame, to prevent the SMA wires from radially exiting the slots and to prevent the wiring and/or piping from radially exiting the hollow spaces.

In FIGS. 8e-8h, the arms and slots are oblique with respect the radial direction. However, the large dimension of the slots 302 has radial component, so that the when the SMA wires move along the large dimensions of the respective slots from the ends of the slots that are closer to the perimeter to the opposite ends, the SMA wires still move inward toward the center. Thus, the distance between the wires and the center of the segments decreases with this motion.

Figure 8E:
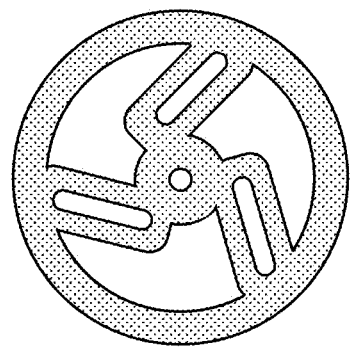
Figure 8F:
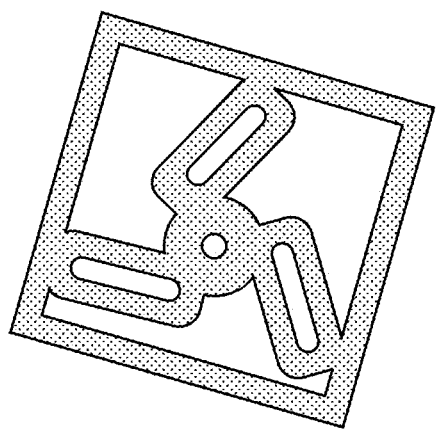
Figure 8G:
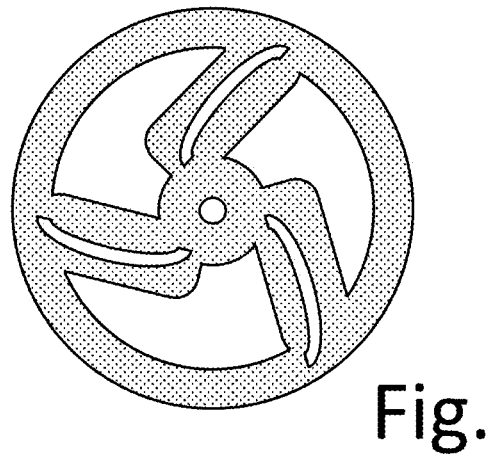
Figure 8H:
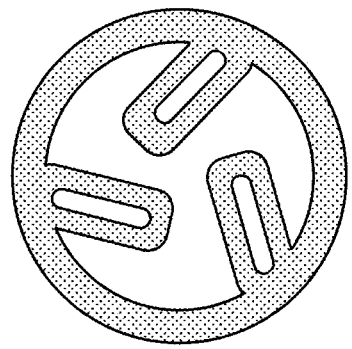
Figure 9:
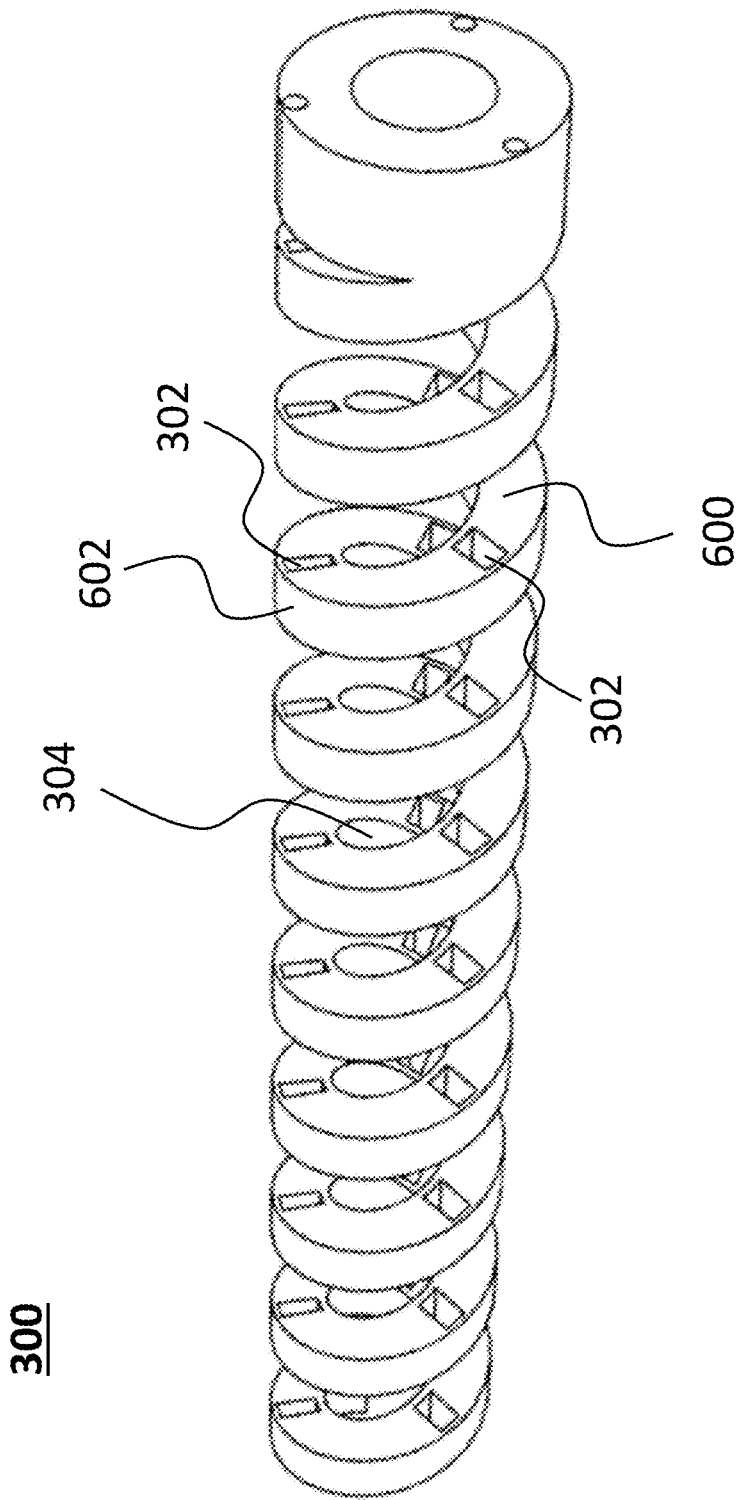
FIG. 9 illustrates a bendable portion of the insertion shaft having a helical frame.

In FIGS. 8e, 8g, and 8h, the segments are circular. In FIG. 8f, the the segment has a polygonal profile. In some embodiments of the present invention, the perimeter of the segments may be any of any shape.

In most figures, the slots have a straight shape. In the example of FIG. 8g (which may be applied to any segment shape), the slots are curved.

Figure 10:
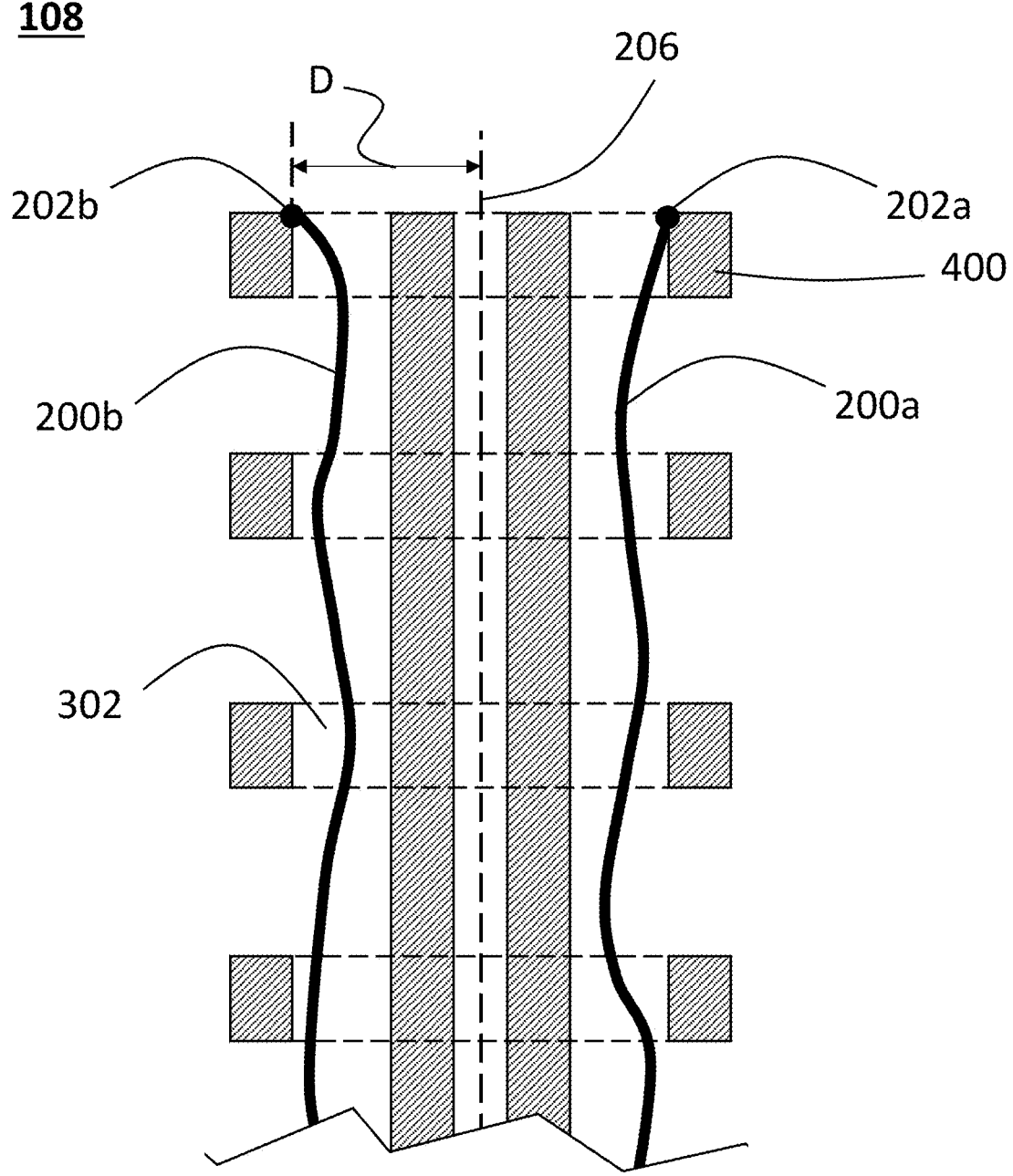
FIGS. 10-12 illustrate different stages of a bending of a bendable portion of the insertion shaft, according to some embodiments of the present invention.
Figure 10:
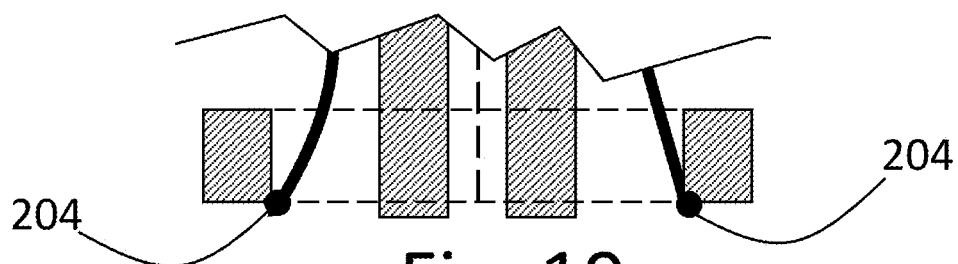
Figure 11:
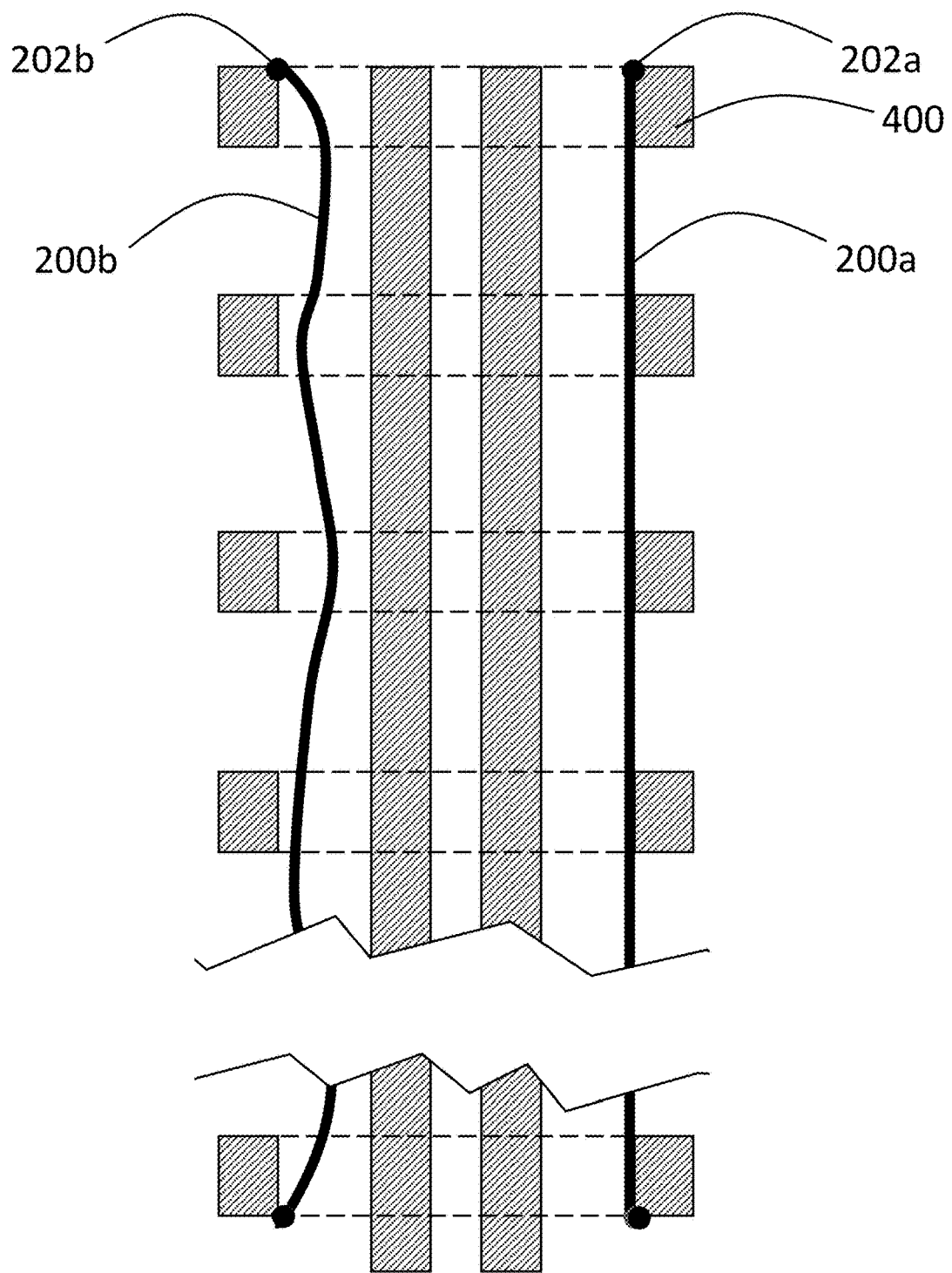
Figure 12:
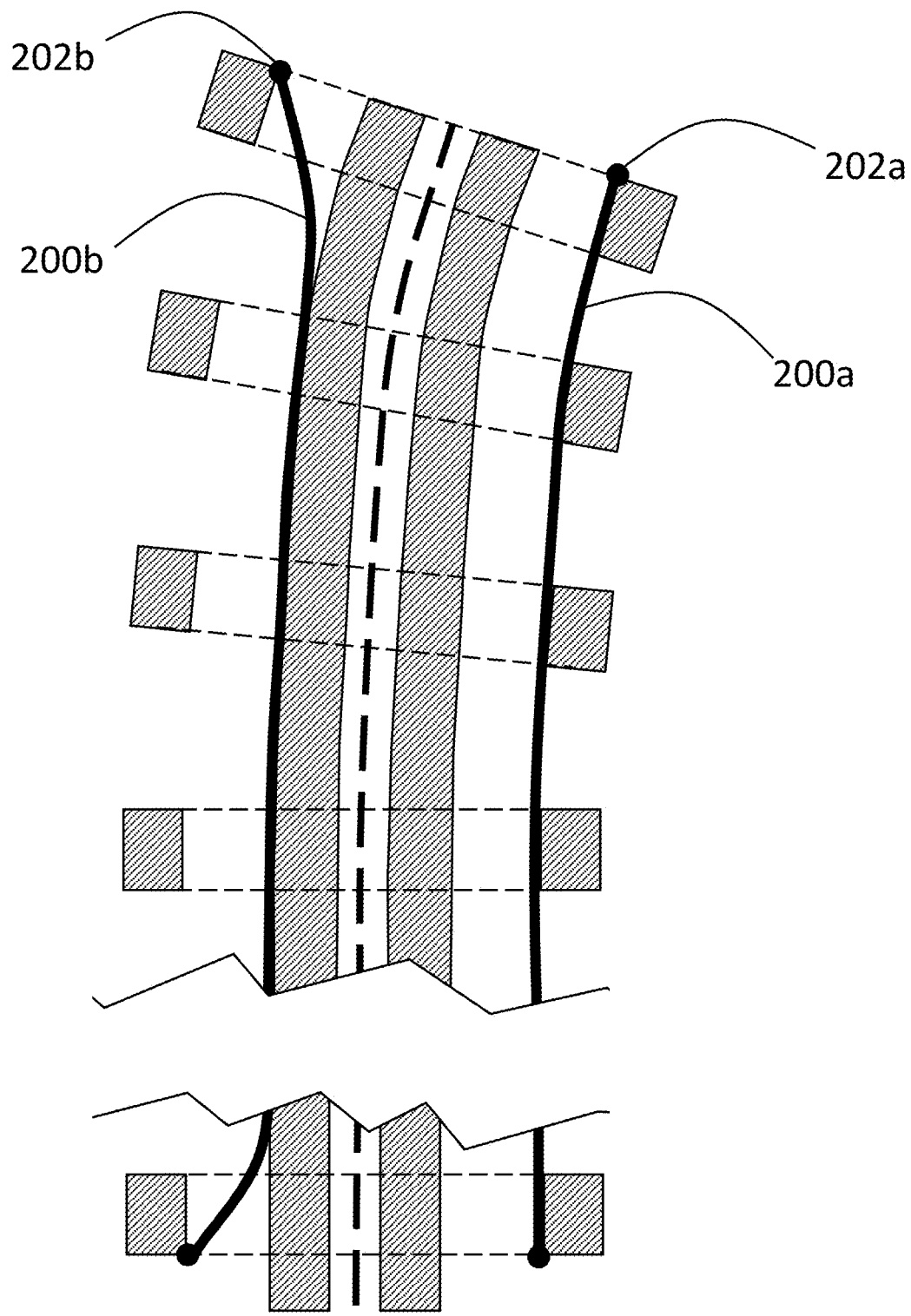

FIGS. 10-12 illustrate different stages of a bending of a bendable portion 108 of the insertion shaft in the embodiments in which the SMA wires have a certain slack and the frame includes slots, according to some embodiments of the present invention. The example of FIG. 10-12 relates to bendable portions having segmented frames. However, the same operation occurs for a helical plane.

The wires 200 are anchored to the distal anchoring points 202 and the proximal anchoring points 204. The anchoring points 202 and 204 are disposed at a distance D from the central axis 206. The distance D is chosen to provide a desired moment arm between the central axis 206 and the SMA wire 200. This is important as some SMA wires (such as nitinol) contract by 3.75%, and a larger moment arm allows a smaller force to produce rotation. In some embodiments of the present invention the distance D is between 2 and 8 mm.

At least a portion of each slot 302 extends from the line of the anchoring points toward the central axis, but end short of the central axis 206.

In FIG. 10, no current is applied to any of the SMA wires 200a, 200b. Both SMA wires are slack, and the slot provide space to store the slack wires.

In FIG. 11, a current is applied to the right-side SMA wire 200a. The right-side SMA wire 200a is therefore heated and begins to contract. If slack is present, part of the contraction is used to eliminate the slack and tense the right-side SMA wire 200a. At this point, the right side SMA wire 200a becomes taught but does not yet apply any force on the respective distal anchoring point 200a.

In FIG. 12, the right-side SMA wire 200a reaches the predetermined temperature for maximal contraction and applies a downward force to its respective distal anchoring point 200a. The top segment 400 rotates clockwise, and the left-side distal anchoring point 200b travels further circumferentially than the right-side distal anchoring pint 200b. On the contracting side, the gaps between the segments decreases, while on the non-contracted side, the gaps between the segments increase. This causes rotation. The non-contracting side now has to travel circumferentially further.

The left-side SMA wire 200b becomes taught, as seen in FIG. 12a. The slots 302 in the segments 400 enable movement of the of the left-side SMA wire 200b toward the central axis 206. This, as the insertion shaft curves, the left-side SMA 200a wire curves at a smaller radius than the distance D. In this manner, a larger amount of slack is reserved for enabling an increase in travel the left side anchoring point 200b. Thus the left-side anchoring point 200b can travel further before the left-side SMA wire 200b reaches its maximal length and prevents further rotation of the top segment 400.

Figure 13:
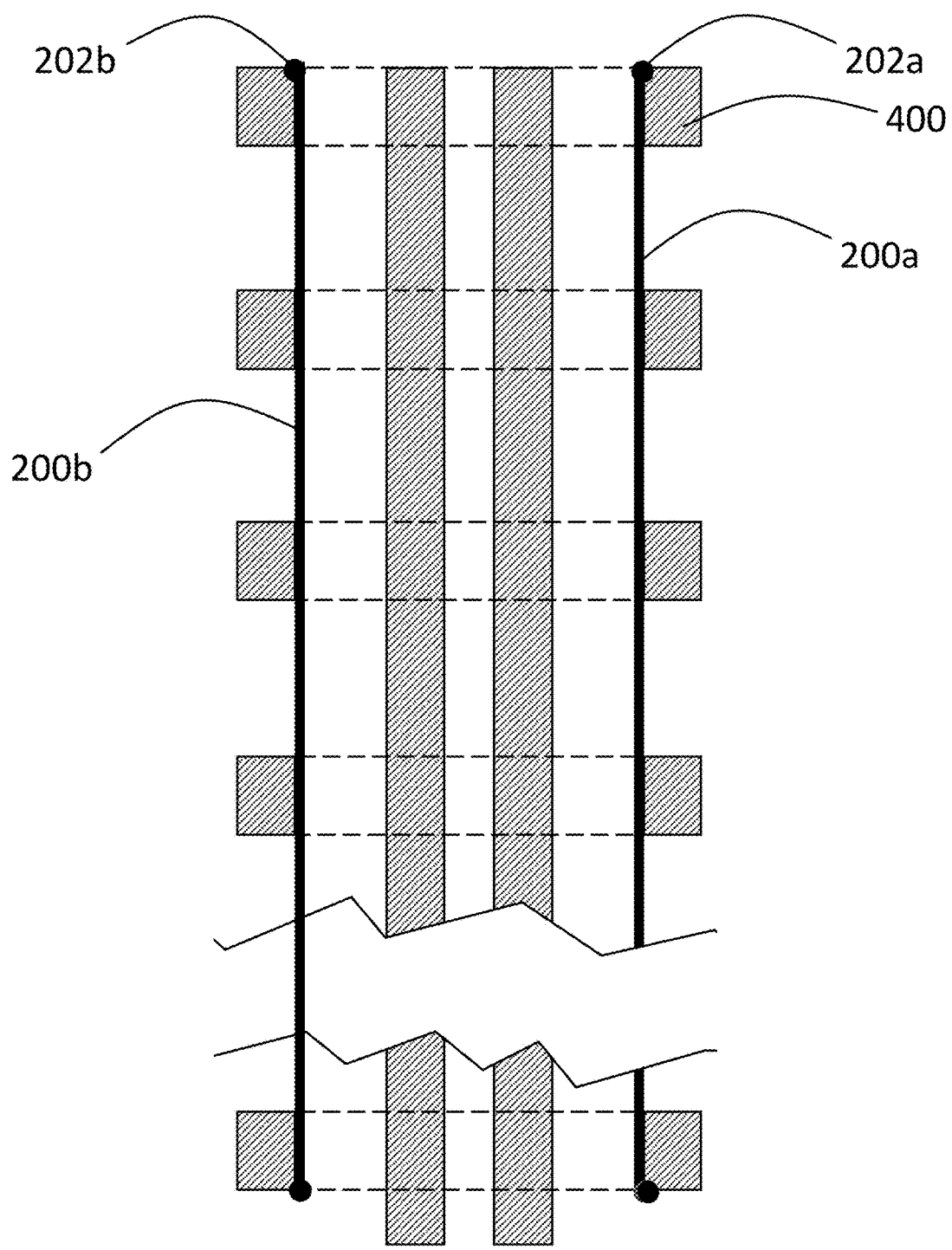
FIGS. 13-14 illustrate different stages of a bending of a bendable portion of the insertion shaft in the embodiments in which the SMA wires have no slack and the frame includes slots, according to some embodiments of the present invention.
Figure 14:
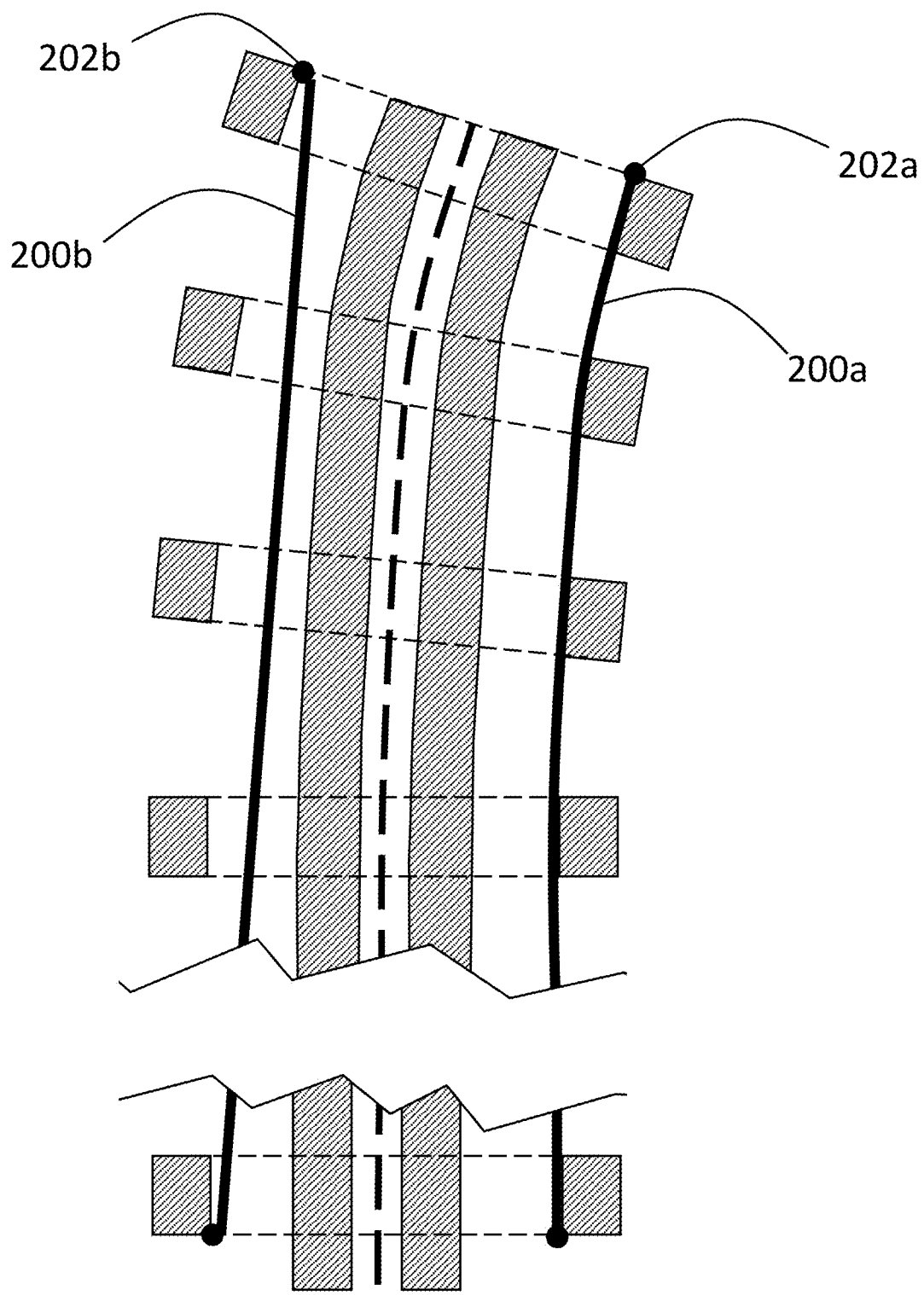

FIGS. 13-14 illustrate different stages of a bending of a bendable portion 108 of the insertion shaft in the embodiments in which the SMA wires have no slack and the frame includes slots, according to some embodiments of the present invention.

In FIG. 13, the SMA wires are not heated. In FIG. 14, the right-side SMA wire 200a is heated and contracts, thereby decreasing the gaps between segments. The left-side SMA wire 200b does not contract and has no slack and therefore remains at the same length. However, the slots enable the left-side wire 200b to approach the central axis. This enables the widening of the gaps between segments on the left-side of the bendable portion 108.

Figure 15C:
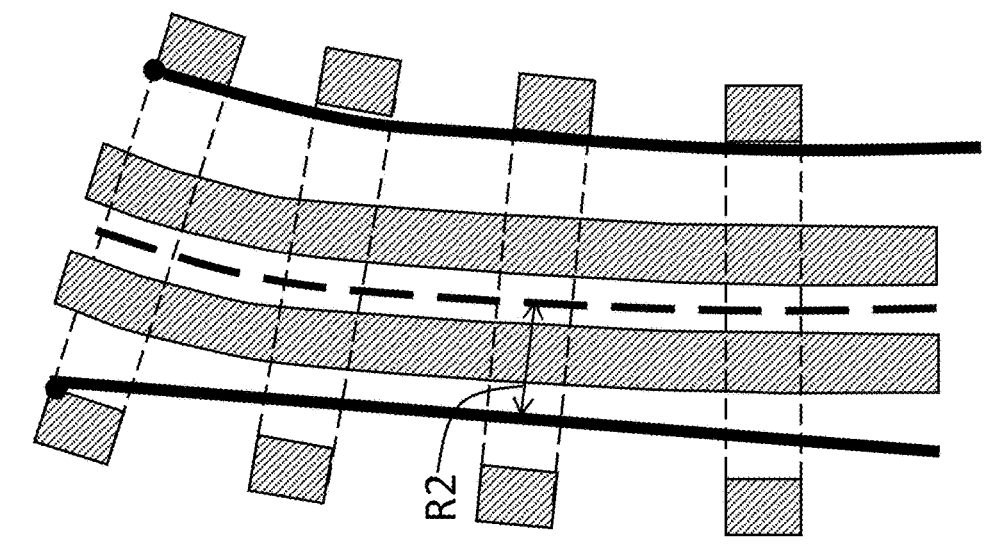
FIGS. 15a-15c are a comparison between bent bendable portion with slots of the present invention and a bent bendable portion with no slots.
Figure 15B:
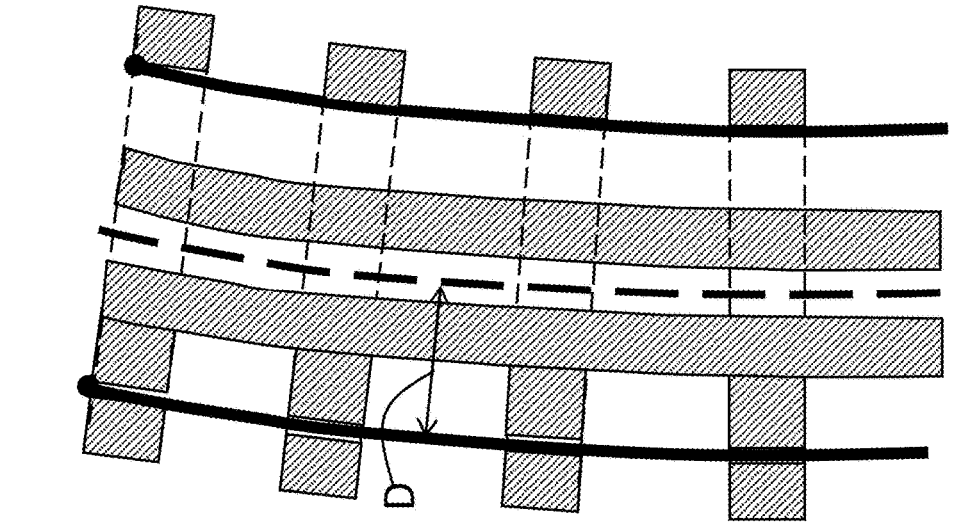
Figure 15A:
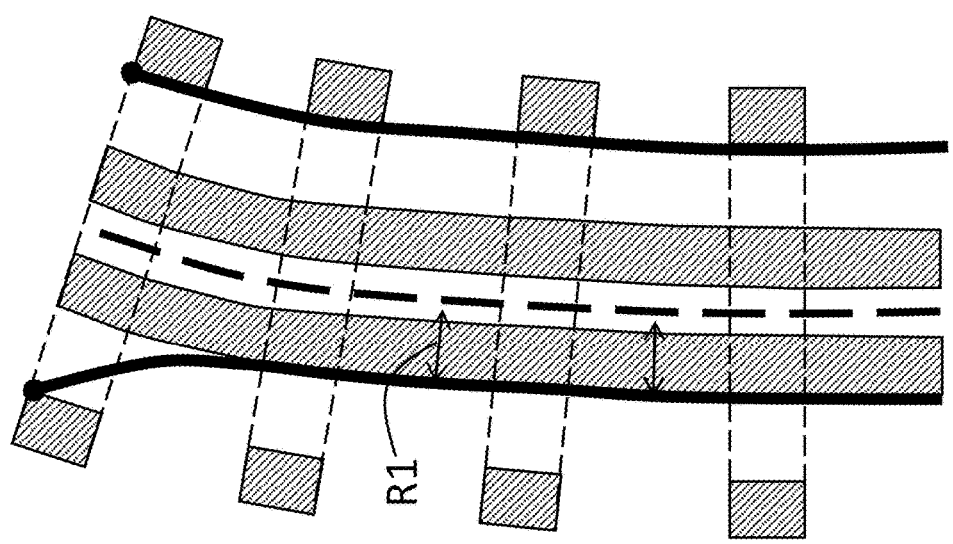

FIGS. 15a-15c shows a comparison among a bent bendable portion with slots and SMA wires with slack of the present invention (15a), a bent bendable portion with no slots and SMA wires with no slack (FIG. 15b), and a bent bendable portion with slots and SMA wires with no slack of the present invention.

In both slotted configurations, the average a radius of curvature (R1 for FIG. 15a and R2 for FIG. 15b), which is smaller than the radius of curvature D (which is the distance between the anchoring point and the central axis) of the left side wire in the slotless configuration. Therefore, in both slotted configuration of the invention, more of the length of the left-side wire can be used to allow clockwise rotation of the top segment.

Though not depicted, it is clear than in the embodiment of the present invention in which the frames do not include slots but the SMA wires have slack, the non-activated wire will follow the curvature D as well. However, due the presence of slack, the fully extended non-activated wire enables an increase in the gaps between segments larger than an increase in the gaps that would be achieved with no slack.

Figure 16:
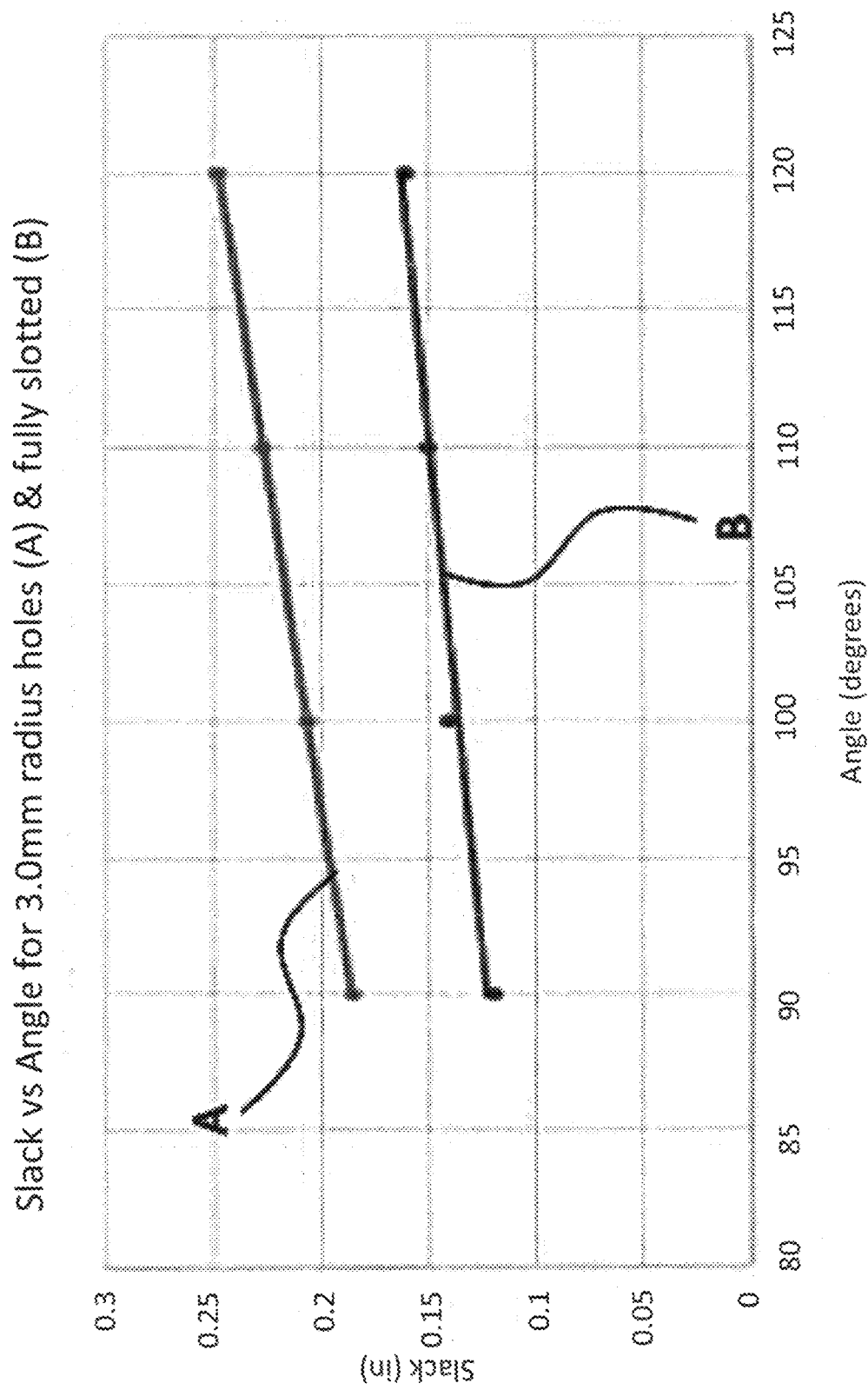
FIG. 16 is a graph showing experimental measurement of the slack needed to rotate a bendable portion using a slotted bendable portion of the present invention and an unslotted bendable portion.

FIG. 16 is a graph showing experimental measurement of the slack needed to rotate a bendable portion using a slotted bendable portion and an unslotted bendable portion.

The unslotted frame had holes in each segment, that were 3 mm away from the center of the segment. The slotted frame had slots extending from 3 mm away from center to 0.5 mm away from center.

It can be easily seen that in order to achieve the same rotation, the bendable portion with slots in the segments needed less slack (about half) of the slack needed by a bendable portion with no slots. This is important, as slack, while advantageous in the non-activated wire, is also partly wasteful, because we part of the contraction of the wire is wasted to bring the activated SMA wire from slack to full tension and does not actively cause flexion of the bendable portion. Therefore, a reduction of the necessary slack enhances the bending efficiency of the insertion shaft of the present invention.

Another advantage of having slots lies in the fact that the SMA wires are more exposed to air in slots that they would be in holes, and therefore cool more quickly after activation ceases. Thus, the wires return to their slack configuration more quickly, thereby enabling quicker activation of other SMAs to change the direction of flexion of the bendable part. Therefore, the slots enhance the responsiveness of the scope.

Figure 17:
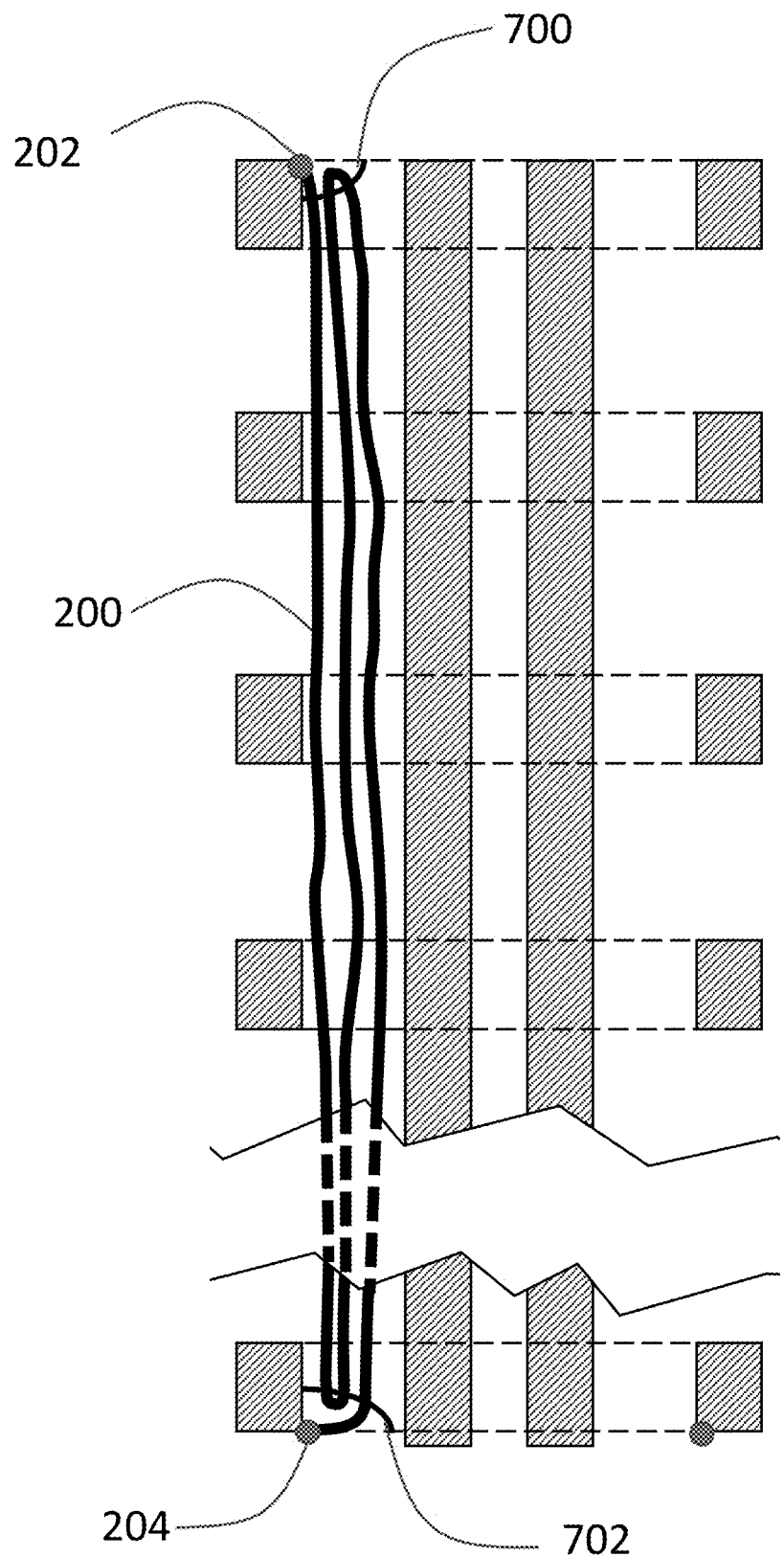
FIG. 17 illustrates an insertion shaft in which at least one of the SMA wires loops about a distal looping point and optionally about a proximal looping point, according to some embodiments of the present invention.

FIG. 17 illustrates an insertion shaft in which at least one of the SMA wires loops about a distal looping point and optionally about a proximal looping point, according to some embodiments of the present invention.

In some embodiments of the present invention, for each SMA wire 200, the bendable portion 108 includes a distal looping 700 point, which may be near the distal anchoring point 202 but can be located anywhere in the insertion shaft. Each wire loops 200 loops about the distal looping point 700 and returns toward the proximal anchoring point. In this manner, each wire can be connected to a respective closed circuit. This eliminates the need for a central grounding wire.

In some embodiments of the present invention, the insertion shaft includes a proximal looping point 702 located between the proximal anchoring point 204 and the distal looping point 700. Each SMA wire 200 loops about the distal looping point 700 and extends to the proximal looping point 702 of the insertion shaft at least once, then loops about the proximal looping point 702 and extends toward the distal looping point 700 at least once. Looping the SMA wires doubles the force applied by the contracting SMA wire on the looping point.

Figure 18:
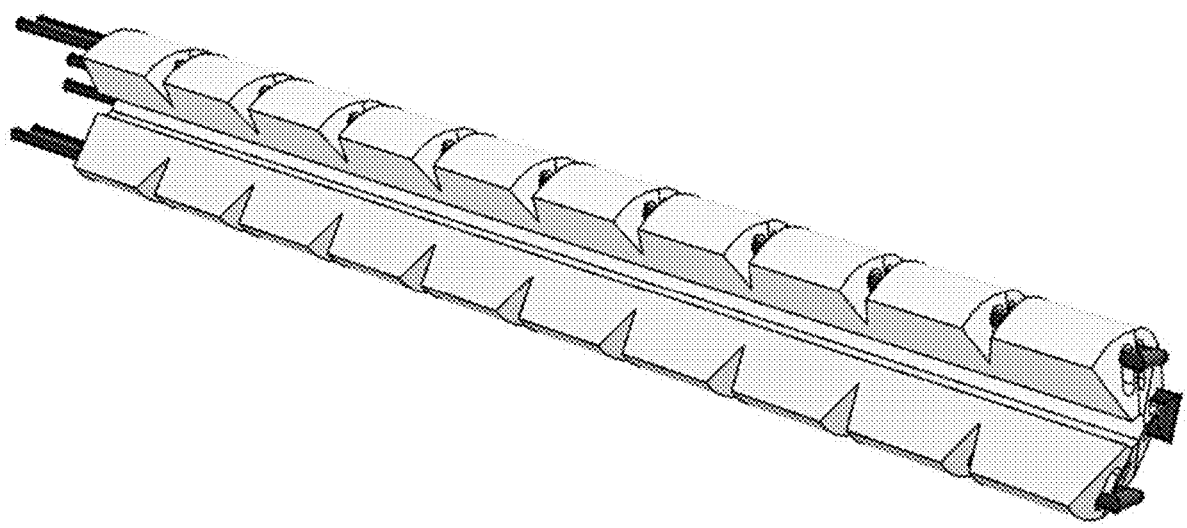
FIG. 18 is a cut view of an insertion shaft with a distal looping point, according to some embodiments of the present invention.

FIG. 18 is a cut view of an insertion shaft with a distal looping point, according to some embodiments of the present invention;

In the example of FIG. 18, the distal looping point 700 is effectively the distal anchoring point. The looping point 700 is formed by two nearby slots or perforations accommodating the SMA wire 200 separated by a wall, such that the SMA wire travels from the proximal anchoring point in one slot or perforation, loops around the distal end of the wall and returns to the proximal anchoring point via the nearby slot or perforation.

FIG. 18 is a perspective view of a flexible central core shaft 800 with a plurality of arms, extending in a portion between the bending portion and the proximal end of the insertion shaft, according to some embodiments of the present invention.

In some embodiment of the present invention, the proximal portion 110 of the insertion shaft includes a flexible central core shaft and a plurality of sets of arms.

The flexible central core shaft 800 extends along the central axis of the insertion shaft. The sets of arms 802 extend substantially radially outward from the central core shaft 800. The sets of arms are spaced apart by respective gaps 804, to enable bending of the flexible central core shaft 800, encourage passive air cooling, and to not impede torque transmission from the proximal end to the distal end of the insertion shaft. In each set of the arms a space between a pair of arms is traversed by a respective SMA wire or by an electrical lead connected to the SMA wire. In this manner, the arms 802 prevent the SMA wires from touching, and enhance the electrical isolation of the SMA wire from each other. Said space between arms may also be traversed by camera wiring and suction tubing, or any other tool of the scope.

The arms of each set may have the same longitudinal dimensions as each other and extend parallel to the central core shaft. Optionally, the longitudinal dimensions of the arms are larger than radial dimensions of the arms. In some embodiments of the present invention, the longitudinal dimensions of the arms are larger than a length of the gap along the central core shaft.

Optionally, the central core shaft 800 has a central perforation, a central elastic wire or spring. In some embodiment of the present invention, the central core and the arms of the segments are integral with each other and made of a single material.

Figure 19:
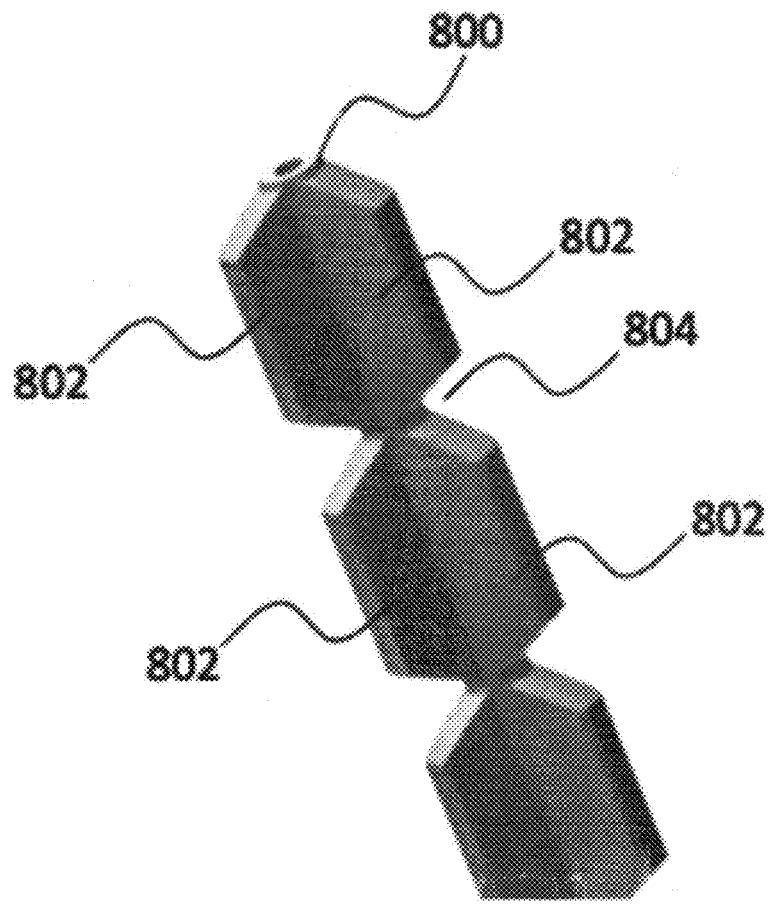
FIGS. 19-21 are a perspective views of a flexible central core shaft with a plurality of arms, extending in a proximal portion between the bending portion and the proximal end of the insertion shaft, according to some embodiments of the present invention.
Figure 20:
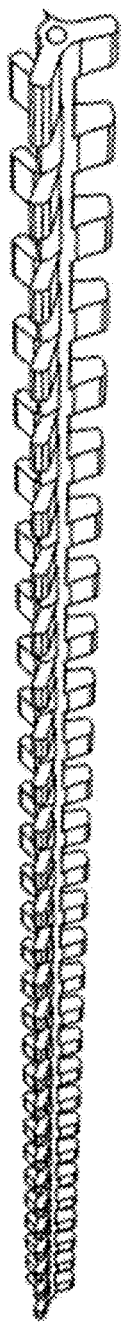
Figure 21:

In the example of FIG. 19, the longitudinal dimensions of the arms are smaller than or equal to a length of the gaps along the central core shaft. In the example of FIG. 19 there are no gaps, and a single set of arms extends along the central core.

Figure 22:
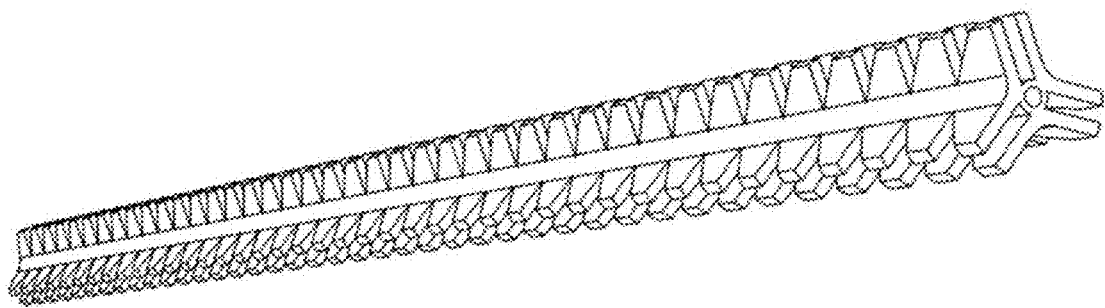
FIGS. 22 and 23 illustrates a flexible central core shaft that runs along the bending portion and the proximal portion of the insertion shaft, according to some embodiments of the present invention.
Figure 23:
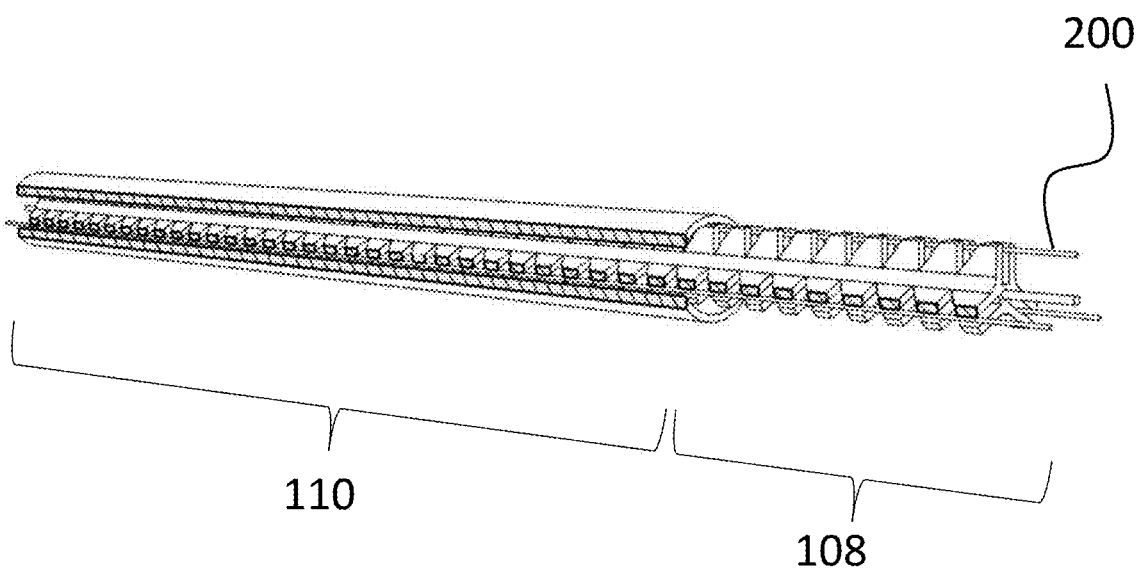

FIGS. 22 and 23 illustrates a flexible central core shaft that runs along the bending portion and the proximal portion of the insertion shaft, according to some embodiments of the present invention.

In some embodiments of the present invention, the central core shaft 800 in the proximal portion 110 is integral with the frame in the bendable portion 108 and has perforations or slots for the passage of SMA wires 200. The proximal portion 110 includes a first sheath 850. The bending portion 108 may have a second sheath (not pictured). The first sheath 850 which is semi-rigid and more resistant to bending than the second sheath. Therefore, the selective contraction of the SMA wires 200 causes bending and flexing at the location of least resistance, which is the bending portion 108.

Figure 24:
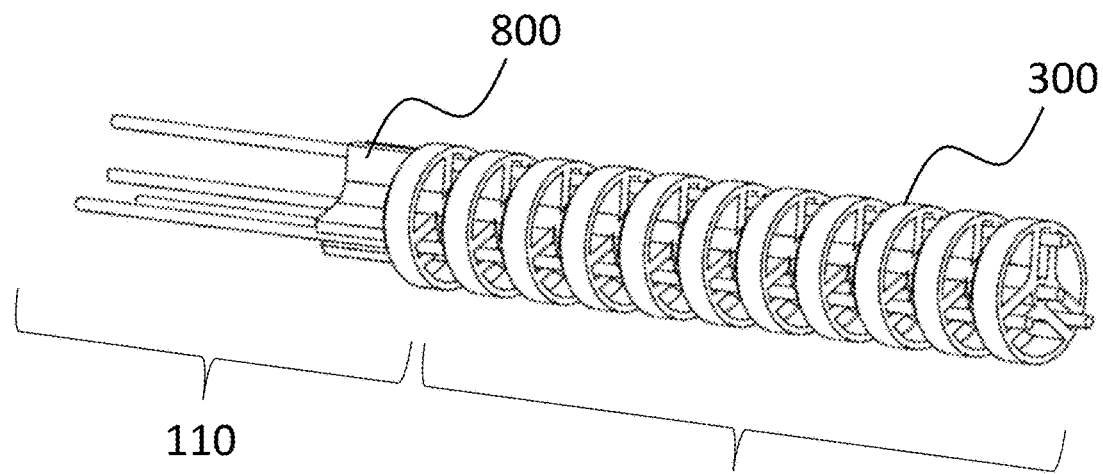
FIG. 24 illustrates an example of a boundary between the central core shaft of the proximal portion of the insertion shaft and a frame of the bendable portion of the insertion shaft, according to some embodiments of the present invention.

FIG. 24 illustrates an example of a boundary between the central core shaft 800 of the proximal portion of the insertion shaft and a frame 300 of the bendable portion the insertion shaft, according to some embodiments of the present invention.

In embodiments, in which the central core shaft 800 of the proximal portion of the insertion shaft and a frame 300 of the bendable portion differ from each other, the distal end of the core shaft 800 is near or attached to the proximal end of the frame 300.

Figure 25:
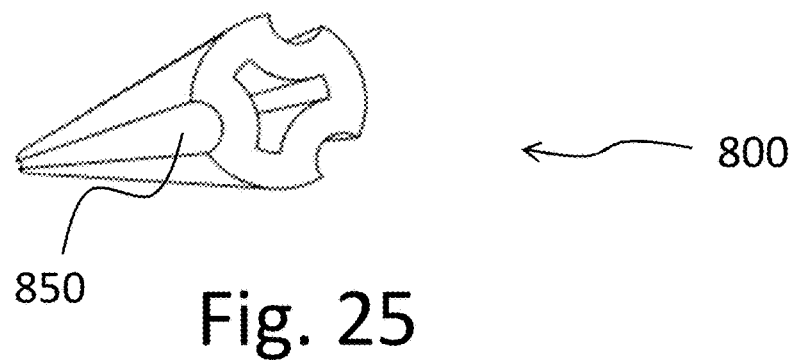
FIGS. 25 and 26 illustrate examples of a notched central core shaft, according to some embodiments of the present invention.
Figure 26:
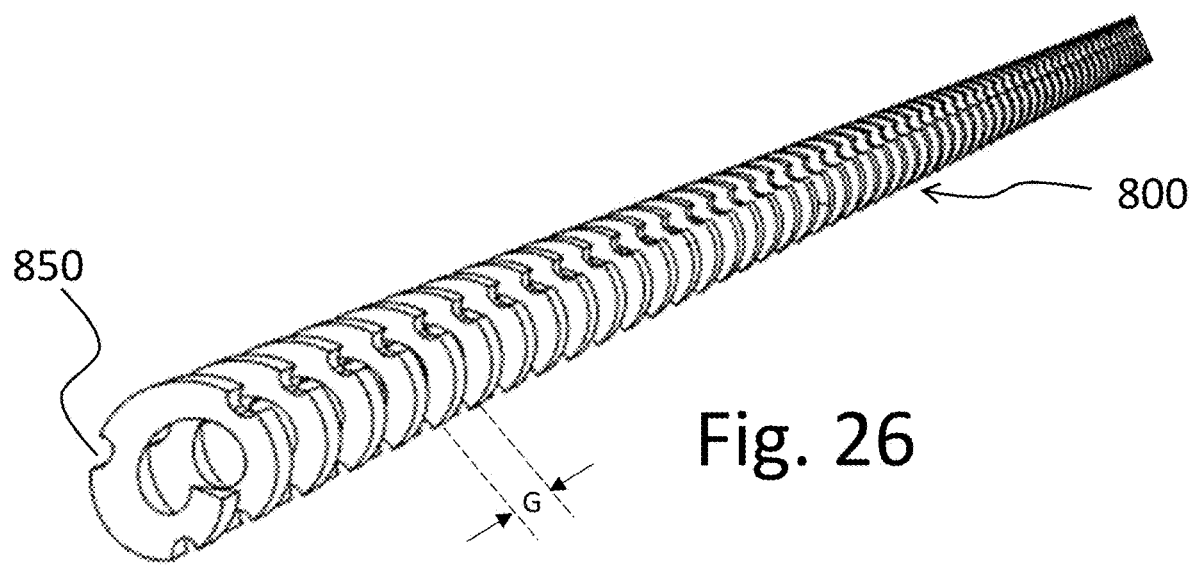

FIGS. 25 and 26 illustrate examples of a notched central core shaft 800, according to some embodiments of the present invention.

In some embodiments, of the present invention, the central core shaft does not have any arms. Rather, notches 850 a present on the perimeter (or circumference) of the central core shaft 800, to accommodate the SMA wires. The central core may have a circular or polygonal profile as seen in FIG. 25. The central core may be helical as seen in FIG. 26. The helical central core provided gaps G for passive cooling of the SMA wires.

It should be noted that for all the central core shafts 800 described above, the wiring and/or tubing for the camera and tools may pass in the middle of the central core shafts along the SMA wires. The specific designs exemplified above may be changed to create or enlarge a middle channel traversing the core shaft, so as to accommodate the required wiring/piping, or to enlarge the spaces traversed by the wires to as to accommodate the requires wiring/piping.

Figure 27:
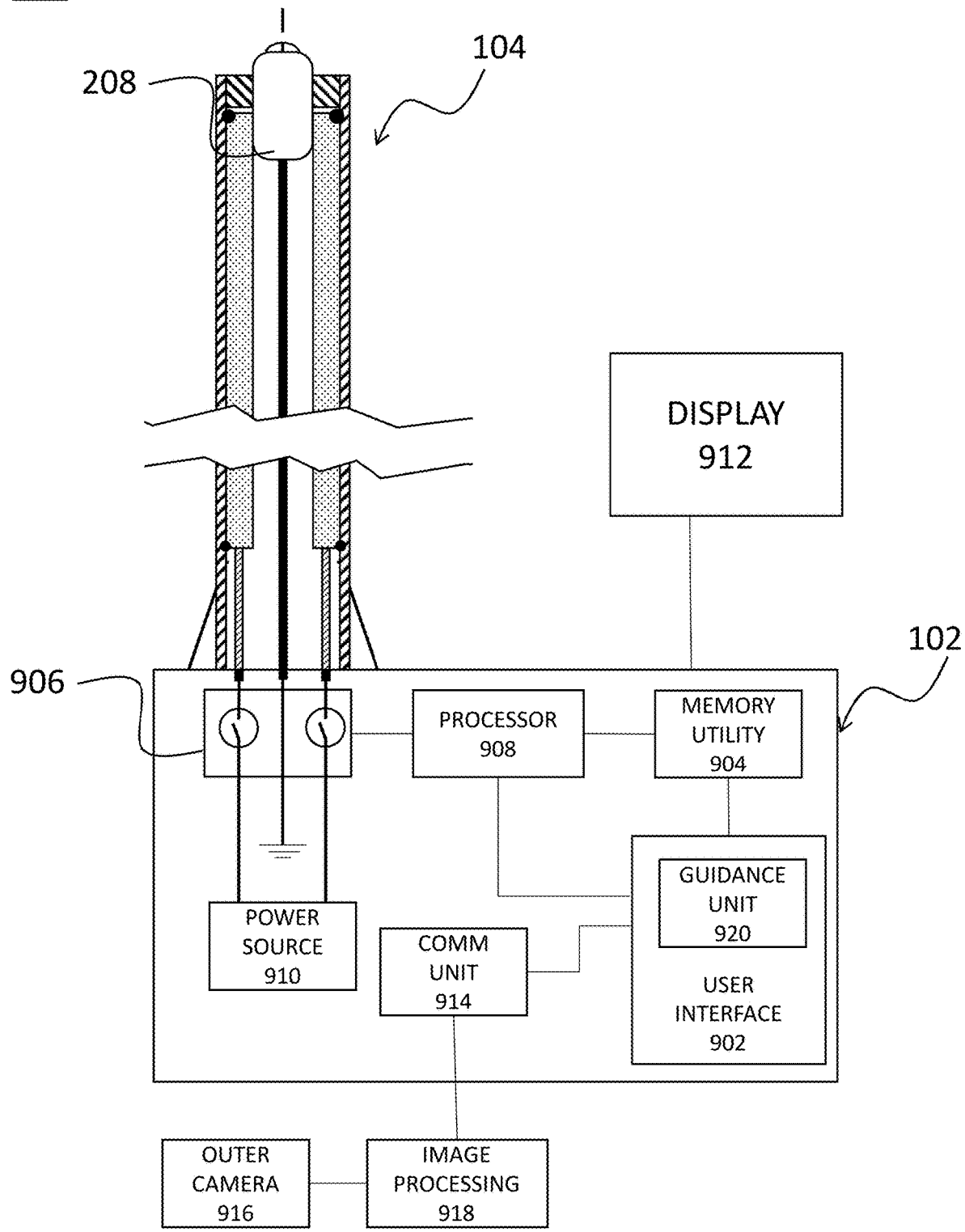
FIGS. 27 and 28 illustrate a scope having an insertion shaft and a control unit, according to some embodiments of the present invention.
Figure 28:
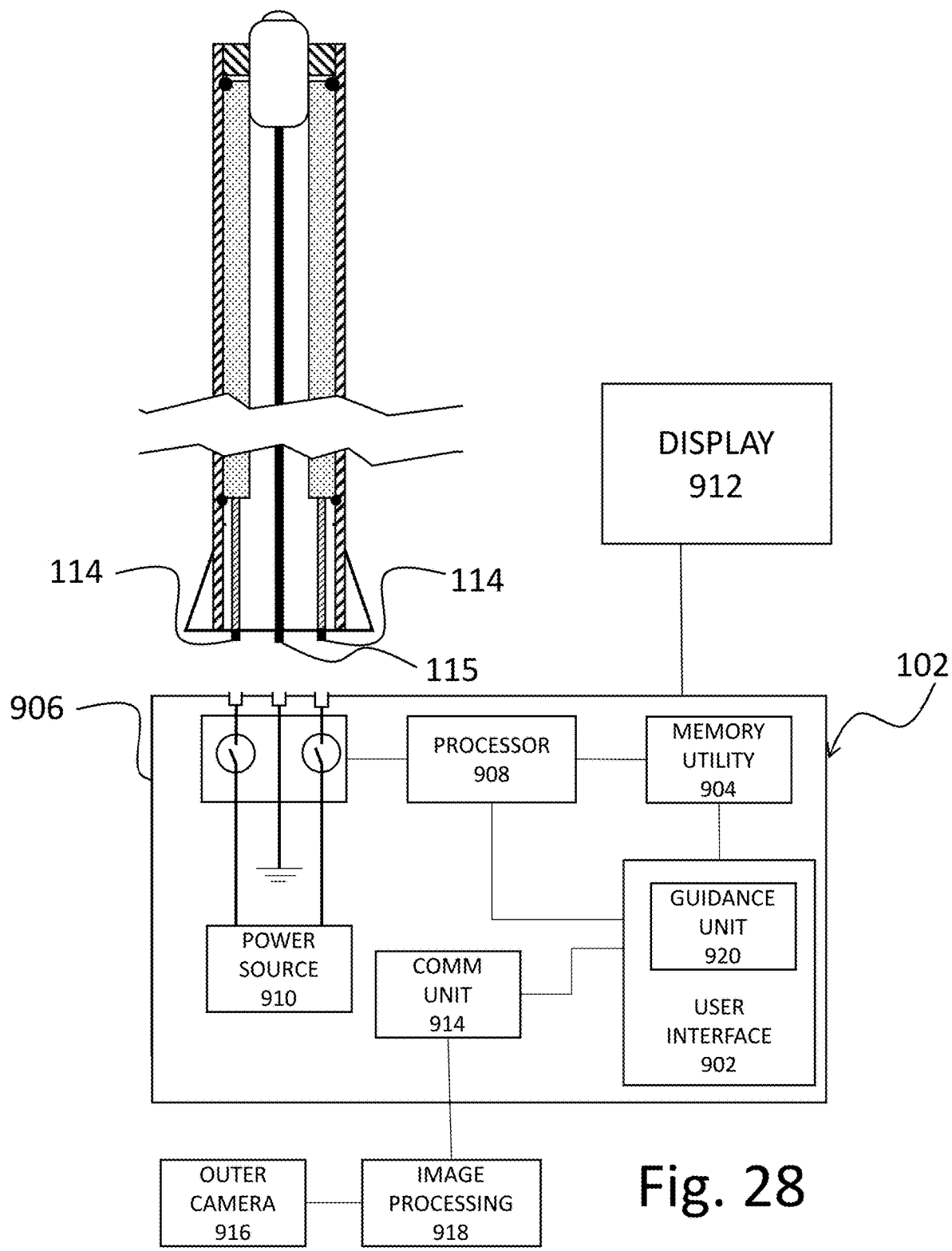

FIGS. 27 and 28 illustrate a scope 100 having an insertion shaft 104 and a control unit 102, according to some embodiments of the present invention.

The insertion shaft 104 has the features described above. The control unit 102 is configured to receive a user instruction to bend the insertion shaft 104 in a desired direction, and to independently and selectively heat each of the SMA wires to the predetermined temperature by applying electrical current via each of the wires, thereby controlling a length of each of the wires. In this manner, a bending of the bendable portion of the insertion shaft is controlled according to the user instruction. It should be noted that, depending on the instructions, the control unit may selectively and independently: apply electrical current to each wire to bring each wire to full contraction; not apply electrical current to each wire to bring the wire to or maintain the wire at the wire's original (uncontracted) lengths; or pulse electrical current through each wire to maintain each wire at an intermediate length between the contracted length and the original (uncontacted) length.

The control unit 102 may include a user interface 902, a non-volatile memory utility 904, a power transmission unit 906, and a processor 908. The user interface 902 is configured for receiving the user instructions. The memory utility 904 is configured to store predetermined commands. The power transmission unit 906 is configured to selectively and independently apply the electrical current from a power source 910 to each one of the SMA wires. The power source may be internal to the control unit (e.g., a battery), or may be external and connectable to the control unit.

The processor 908 is configured to receive the user instructions and to use the predetermined commands to translate the user instructions to generate control signals that control an operation of the power transmission unit 906, in order to bend the insertion shaft according to the user instructions.

In some embodiments of the present invention, the scope includes a camera 208 located at the distal portion of the insertion shaft 104. The camera is configured to capture an image and generate electrical signals indicative of the image. The control unit is configured to be connected to a display 912 by wire or wirelessly, and to transmit the electrical signals from the camera to the display 912, to enable the display to display the image.

In some embodiments of the present invention, the scope includes the display 912. The display is configured to be removably joined to the control unit 102.

In a variant, the insertion shaft 104 comprises a connector at the proximal end thereof and is removably joined to the control unit via the connector, as explained above. The connector includes electrical connection pins 114 to connect the SMA wires to the power transmission unit 906. Optionally, if a central grounding wire is present, a respective electrical connection pin 115 is configured to connect the central grounding wire to an electrical ground.

In a variant, the user interface comprises a joystick 902. The joystick may be part of the control unit 102, or may be a remote joystick connectable to the user interface via a communication unit 914.

Figure 29:
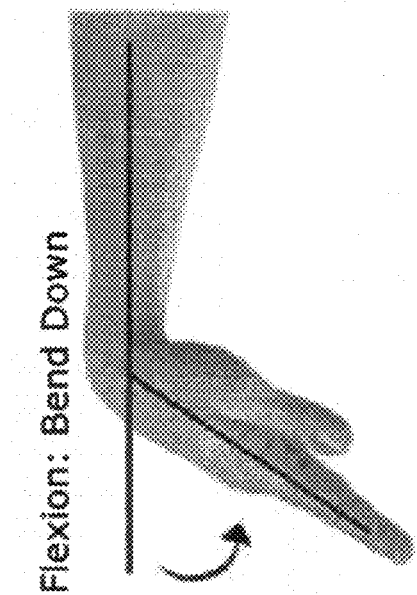
FIG. 29 illustrates and example of hand signals than can be used as instructions for controlling the bending of the insertion shaft, according to some embodiments of the present invention.
Figure 29:
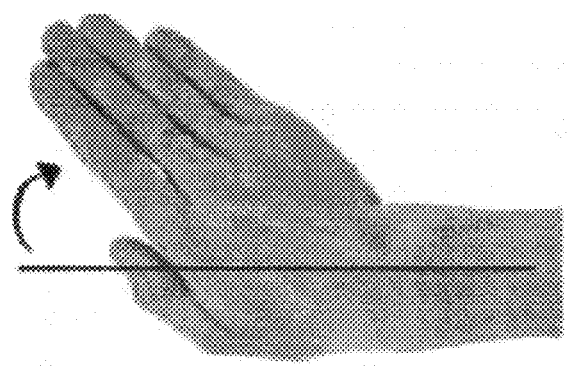
Figure 29:
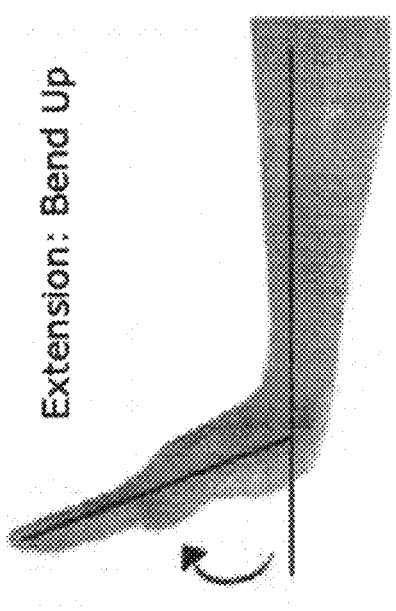
Figure 29:
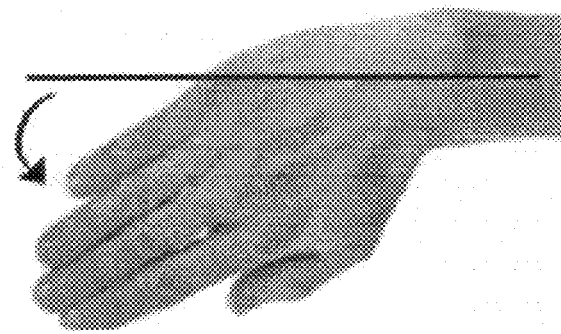

In some embodiments of the present invention, the user interface includes or is connectable to an outer camera 916 and an image processing unit 918. The outer camera 916 is configured to capture hand signals of a user, and the image processing unit 918 is configured to translate hand signals into electronic signals for bending the shaft. The translated hand signals reach are transmitted to the processor for controlling the bending of the insertion shaft. Non-limiting example of hands signals corresponding to certain user instructions is shown in FIG. 29.

In some embodiments of the present invention, the user interface includes or is connectable to the camera 218 located at a distal portion of the insertion shaft and pointing ahead of the insertion shaft, and includes a guidance unit 920 configured to keep the camera pointed to toward a center of a lumen in which the insertion shaft travels. The guidance unit 920 processes the images from the camera 218 and calculates a desired bending instruction to automatically bend the shaft to keep the camera pointing forward throughout the travel of the shaft. The desired bending instructions are sent to the processor, which generates the control signals accordingly.

What is claimed is:

1. An insertion shaft for an electrically actuated scope, the insertion shaft comprising:
    at least two shape-memory-alloy (SMA) wires having proximal ends each anchored to a respective proximal anchoring point located at a proximal end of the insertion shaft or at a predetermined location along the insertion shaft and having distal ends each anchored to a respective distal anchoring point located between a distal end of the insertion shaft and the proximal anchoring points, the SMA wires being disposed around a central axis and extending along the insertion shaft, wherein each of the SMA wires comprises two-way memory material configured to contract when heated to or above a first predetermined temperature and return to a predetermined original length thereof upon cooling to or below a second predetermined temperature below the first predetermined temperature;
    wherein for each of the SMA wires, a length of the SMA wire between the proximal anchoring point and the distal anchoring point to which the wire is anchored is larger than a length of the insertion shaft between the proximal anchoring point and the distal anchoring point to which the SMA wire is anchored, such that each of the SMA wires is incorporated in the insertion shaft with a predetermined slack;
    wherein the insertion shaft is configured to be joined to a control apparatus, such that each SMA wire is configured to be independently and selectively heated by application of electrical current from the control apparatus, to yield a bending of the bendable portion.

2. The insertion shaft of claim 1, further comprising a central wire or central spring disposed along the central axis, the central wire or central spring being elastic, such that the central wire or central spring is configured to maintain the insertion shaft unbent when all the SMA wires are at or below the second predetermined temperature.

3. The insertion shaft of claim 2, wherein the central wire or central spring is a grounding wire electrically connected to the SMA wires and configured to be connected to an electrical ground.

4. The insertion shaft of claim 1, wherein a bendable portion of the insertion shaft located between the proximal anchoring point and the distal anchoring point comprises a frame, comprising:
    a plurality of discrete slots, each slot being elongated and having a large dimension and a small dimension, the large dimension extending radially or with a radial component from the central axis, each slot being traversed by a respective one of the SMA wires and enabling movement of the SMA wire along the large dimension; and
    one or more hollow spaces configured to be traversed by wiring and/or piping for tools held by the insertion shaft.

5. The insertion shaft of claim 4, wherein the frame comprises a plurality of segments spaced-apart along the central axis of the insertion shaft, each segment comprising:
    a central hub located in middle of the segment and centered about the central axis of the insertion shaft;
    a plurality of arms extending radially or with a radial component outward from the central hub, the slots being carved out of the arms;
    wherein the hollow spaces are disposed between the arms; and
    wherein a distance between the segments is selected to enable an orientation change between successive segments.

6. The insertion shaft of claim 5, further comprising a central wire or central spring disposed along the central axis, the central wire or central spring being elastic, such that the central wire or central spring is configured to maintain the insertion shaft unbent when all the SMA wires are at or below the second predetermined temperature;
    wherein the central hub of each segment has a central perforation configured to be traversed by the central wire or central spring.

7. The insertion shaft of claim 4, wherein the frame comprises a plurality of segments spaced-apart along the central axis of the insertion shaft, each segment comprising:
a plurality of arms extending radially or with a radial component inward from a perimeter of the frame, the slots being carved out of the arms;
wherein the hollow spaces are disposed between the arms.

8. The insertion shaft of claim 7, wherein any two successive segments share a central core and are separated by a gap extending radially from the perimeter of the frame toward the central core.

9. The insertion shaft of claim 4, wherein the frame is helical and has a radial thickness extending inward from a perimeter to the frame, such that the slots are carved out of the radial thickness.

10. The insertion shaft of claim 4 wherein the slots have straight or curved shapes.

11. The insertion shaft of claim 4, wherein the frame has a continuous perimeter ridge which encloses the slots and the hollow spaces.

12. The insertion shaft of claim 4 wherein:
the frame has a non-continuous perimeter ridge which encloses the hollow spaces, but is open at the slots;
the insertion shaft comprises a flexible outer sheath enclosing the frame, to prevent the SMA wires from radially exiting the slots.

13. The insertion shaft of claim 4, wherein:
the frame has a non-continuous perimeter ridge which encloses the slots, but is open at the hollow spaces;
the insertion shaft comprises a flexible outer sheath enclosing the segments, to prevent the wiring and/or piping from radially exiting the hollow spaces.

14. The insertion shaft of claim 4, wherein a portion between the bending portion and the proximal end of the insertion shaft comprises:
a flexible central core shaft extending along the central axis of the insertion shaft and configured for guiding the SMA wires therethrough.

15. The insertion shaft of claim 14, further comprising:
a plurality of sets of arms extending radially or with a radial component outward from the central core shaft, the arms having same longitudinal dimensions extending parallel to the central core shaft;
the sets of arms are spaced apart by respective gaps;
wherein in each set of the arms a space between a pair of arms is traversed by a respective SMA wire or by an electrical lead connected to the SMA wire.

16. The insertion shaft of claim 14, wherein the central core shaft has a central perforation.

17. The insertion shaft of claim 14, wherein the central core shaft and frame are integral with each other.

18. The insertion shaft of claim 1, wherein each SMA wire loops about a respective distal looping point and returns toward the respective proximal anchoring point.

19. The insertion shaft of claim 1, wherein at least one of the SMA wires is in a form a helical coil extending parallel to the central axis.

20. The insertion shaft of claim 1, comprising at least three SMA wires.

21. The insertion shaft of claim 1, comprising an electrical valve configured to control an operation of a suction line joined to the insertion shaft, the electrical valve being configured to be connected to the control unit and to be controlled by the control unit.

22. A scope, comprising:
the insertion shaft of claim 1; and
a control unit configured to receive a user instruction to bend the insertion shaft in a desired direction, and to independently and selectively heat each of the SMA wires to the predetermined temperature by applying electrical current via each of the SMA wires, thereby controlling a length of each of the SMA wires, to control a bending of the bendable portion of the insertion shaft according to the user instruction.

23. The scope of claim 22, wherein the control unit comprises:
a user interface, for receiving the user instructions;
a memory utility configured to store predetermined commands;
a power transmission unit configured to selectively and independently apply the electrical current to each one of the SMA wires;
a processor, configured to receive the user instructions and to use the predetermined commands to translate the user instructions to generate control signals that controls an operation of the power transmission unit in order to bend the insertion shaft according to the user instructions.

24. The scope of claim 22, comprising a camera located at the distal end of the insertion shaft, the camera being configured to capture an image and generate electrical signals indicative of the image;
wherein the control unit is configured to be connected to a display by wire or wirelessly, and to transmit the electrical signals from the camera to the display, to enable the display to display the image.

25. The scope of claim 24, comprising the display, wherein the display is configured to be removably joined to the control unit.

26. The scope of claim 22, wherein the insertion shaft comprises a connector at the proximal end thereof and is removably joined to the control unit via the connector.

27. The scope of claim 23, wherein the user interface comprises a camera configured to capture hand signals of a user, with an image processing unit configured to translate the hand signals captured by the camera into electronic signals for bending the shaft.

28. The scope of claim 23, wherein the user interface comprises:
a camera located at a distal end of the insertion shaft and pointing ahead of the insertion shaft; and
an image processing unit configured to keep the camera to be centered in a lumen in which the insertion shaft travels, and to automatically bend the shaft to maintain the camera position in the center of the lumen throughout the travel of the lumen.

29. An insertion shaft for an electrically actuated scope, the insertion shaft comprising:
at least two SMA wires having proximal ends each anchored to a respective proximal anchoring point located at a proximal end of the insertion shaft or at a predetermined location along the insertion shaft and having distal ends each anchored to a respective distal anchoring point located between a distal end of the insertion shaft and the proximal anchoring point, the SMA wires being disposed around a central axis and extending along the insertion shaft, wherein each of the wires comprises two-way memory material configured to contract when heated to or above a first predetermined temperature and return to a predetermined original length thereof upon cooling to or below a second predetermined temperature below the first predetermined temperature;

wherein a bendable portion of the insertion shaft located between the proximal anchoring point and the distal anchoring point comprises a frame, comprising:
- a plurality of discrete slots, each slot being elongated and having a large dimension and a small dimension, the large dimension extending radially or with a radial component from the central axis, each slot being traversed by a respective one of the SMA wires and enabling movement of the SMA wire along the large dimension; and
- one or more hollow spaces configured to be traversed by wiring and/or piping for tools held by the insertion shaft;

wherein the insertion shaft is configured to be joined to a control apparatus, such that each SMA wire is configured to be independently and selectively heated by application of electrical current from the control apparatus, to yield a bending of the bendable portion.

30. The insertion shaft of claim 29, wherein for each of the SMA wires, a length of the SMA wire is larger between the proximal anchoring point and the distal anchoring point to which the wire is anchored than a length of the insertion shaft between the proximal anchoring point and the distal anchoring point to which the SMA wire is anchored, such that each of the SMA wires is incorporated in the insertion shaft with a predetermined slack.

* * * * *